US008401873B2

(12) United States Patent
Brown et al.

(10) Patent No.: US 8,401,873 B2
(45) Date of Patent: Mar. 19, 2013

(54) HEALTH DATA MANAGEMENT DEVICE

(75) Inventors: Darren Brown, Harrison, NY (US); Jun Chen, Warren, NJ (US); Igor Gofman, Croton-on-Hudson, NY (US); Steven B. Harris, Briarcliff Manor, NY (US); Paul L. Inman, Nyack, NY (US); Richard Kates, Ridgewood, NJ (US); Qiong Li, Tappan, NY (US); Harris Lieber, White Plains, NY (US); Paul M. Ripley, Nanuet, NY (US); Gregory Stefkovic, Mahopac, NY (US); Hoi-Cheong Steve Sun, Mount Kisco, NY (US); Mu Wu, Hopewell Junction, NY (US); Raymond Yao, Tarrytown, NY (US); Simin Yao, Boonton Township, NJ (US)

(73) Assignee: Bayer HealthCare LLC, Tarrytown, NY (US)

( * ) Notice: Subject to any disclaimer, the term of this patent is extended or adjusted under 35 U.S.C. 154(b) by 795 days.

(21) Appl. No.: 12/129,562

(22) Filed: May 29, 2008

(65) Prior Publication Data

US 2008/0300920 A1    Dec. 4, 2008

Related U.S. Application Data

(60) Provisional application No. 60/932,286, filed on May 30, 2007, provisional application No. 61/012,721, filed on Dec. 10, 2007, provisional application No. 61/012,718, filed on Dec. 10, 2007.

(51) Int. Cl.
*G06Q 10/00* (2012.01)
(52) U.S. Cl. ............................................... 705/3; 705/2
(58) Field of Classification Search ................... 705/2, 3
See application file for complete search history.

(56) References Cited

U.S. PATENT DOCUMENTS 3,578,405 A   5/1971  Woodle
4,482,261 A   11/1984 Dewey et al.
4,560,286 A   12/1985 Wickersheim
(Continued)

FOREIGN PATENT DOCUMENTS

EP    0 851 229    1/1998
EP    1087217     3/2001
(Continued)

OTHER PUBLICATIONS

Desautels G. L. et al.: "Optical Temperature Sensor and Thermal Expansion Measurement Using a Femtosecond Micromachined Grating in 6H-SiC", Applied Optics, OSA, Optical Society of America, Washington, D.C.; vol. 47, No. 21 (Jul. 20, 2008); pp. 3773-3777).

(Continued)

*Primary Examiner* — Robert Morgan
*Assistant Examiner* — Maroun Kanaan
(74) *Attorney, Agent, or Firm* — Nixon Peabody LLP

(57) ABSTRACT

A device for managing health data provides a first housing portion including a data storage system that stores health data and a second housing portion including a data communications element. The data communications element provides data communications between the data storage system and a processing device that processes the health data according to a data-management software. The first housing portion and the second housing portion are connected by a cable that communicates signals between the data communications element and other components in the first housing portion. Another device for managing health data provides a first housing portion including a health data management system and a data communications element that provides data communications between the health data management system and an external processing device. The second housing portion is removably coupled to the first housing portion, and includes at least one component used by the health data management system.

14 Claims, 16 Drawing Sheets

U.S. PATENT DOCUMENTS

| | | | |
|---|---|---|---|
| 4,718,777 A | 1/1988 | Mydynski et al. |
| 4,741,476 A | 5/1988 | Russo et al. |
| 4,836,442 A | 6/1989 | Beckey |
| 4,935,345 A | 6/1990 | Guilbeau et al. |
| 5,001,656 A | 3/1991 | Zimmerman et al. |
| 5,199,637 A | 4/1993 | Adams |
| 5,304,405 A | 4/1994 | Kobayashi et al. |
| 5,304,495 A | 4/1994 | Yim |
| 5,405,511 A | 4/1995 | White et al. |
| 5,626,139 A | 5/1997 | Szeles et al. |
| 5,972,715 A | 10/1999 | Celentano et al. |
| 6,063,233 A | 5/2000 | Collins et al. |
| 6,068,400 A | 5/2000 | Nelson et al. |
| 6,144,869 A | 11/2000 | Berner et al. |
| 6,233,471 B1 | 5/2001 | Berner et al. |
| 6,238,085 B1 | 5/2001 | Higashi et al. |
| 6,283,628 B1 | 9/2001 | Goodwin |
| 6,356,776 B1 | 3/2002 | Berner et al. |
| 6,391,645 B1 | 5/2002 | Huang et al. |
| 6,594,514 B2 | 7/2003 | Berner et al. |
| 6,595,919 B2 | 7/2003 | Berner et al. |
| 6,635,167 B1 | 10/2003 | Batman et al. |
| 6,645,368 B1 | 11/2003 | Beaty et al. |
| 6,780,296 B1 | 8/2004 | Bhullar et al. |
| 6,787,109 B2 | 9/2004 | Haar et al. |
| 6,816,537 B2 | 11/2004 | Liess |
| 6,825,044 B2 | 11/2004 | Zheng et al. |
| 6,850,790 B2 | 2/2005 | Berner et al. |
| 6,866,758 B2 | 3/2005 | Bhullar et al. |
| 6,880,968 B1 | 4/2005 | Haar |
| 6,898,451 B2 | 5/2005 | Wuori |
| 7,174,199 B2 | 2/2007 | Berner et al. |
| 7,295,867 B2 | 11/2007 | Berner et al. |
| 7,338,637 B2 | 3/2008 | Pease et al. |
| 7,338,639 B2 | 3/2008 | Burke et al. |
| 7,361,830 B2 | 4/2008 | Richetto et al. |
| 7,364,353 B2 | 4/2008 | Kolk |
| 7,375,494 B2* | 5/2008 | Daniel et al. ................. 320/112 |
| 7,390,667 B2 | 6/2008 | Burke et al. |
| 7,407,811 B2 | 8/2008 | Burke et al. |
| 7,452,457 B2 | 11/2008 | Burke et al. |
| 7,460,958 B2 | 12/2008 | Walsh et al. |
| 7,480,032 B2 | 1/2009 | Braig et al. |
| 2002/0081231 A1 | 6/2002 | Shapiro et al. |
| 2003/0064525 A1 | 4/2003 | Liess |
| 2003/0153821 A1 | 8/2003 | Berner et al. |
| 2003/0160155 A1 | 8/2003 | Liess |
| 2003/0175806 A1 | 9/2003 | Rule et al. |
| 2004/0005716 A9 | 1/2004 | Beaty et al. |
| 2004/0059235 A1 | 3/2004 | Saadat |
| 2004/0132171 A1 | 7/2004 | Rule et al. |
| 2004/0152956 A1 | 8/2004 | Korman |
| 2004/0157337 A1 | 8/2004 | Burke et al. |
| 2004/0157338 A1 | 8/2004 | Burke et al. |
| 2004/0157339 A1 | 8/2004 | Burke et al. |
| 2004/0157638 A1* | 8/2004 | Moran et al. ................. 455/550.1 |
| 2004/0167801 A1 | 8/2004 | Say et al. |
| 2004/0238357 A1 | 12/2004 | Bhullar et al. |
| 2004/0256248 A1 | 12/2004 | Burke et al. |
| 2004/0259180 A1 | 12/2004 | Burke et al. |
| 2004/0260511 A1 | 12/2004 | Burke et al. |
| 2005/0009101 A1 | 1/2005 | Blackburn |
| 2005/0070771 A1 | 3/2005 | Rule et al. |
| 2005/0148003 A1 | 7/2005 | Keith et al. |
| 2006/0004267 A1 | 1/2006 | Rule et al. |
| 2006/0020179 A1 | 1/2006 | Anderson et al. |
| 2006/0085137 A1 | 4/2006 | Bartkowiak et al. |
| 2006/0133960 A1 | 6/2006 | Ahmad |
| 2006/0156796 A1 | 7/2006 | Burke et al. |
| 2006/0229502 A1 | 10/2006 | Pollock et al. |
| 2007/0038053 A1 | 2/2007 | Berner et al. |
| 2007/0106135 A1 | 5/2007 | Sloan et al. |
| 2007/0142721 A1 | 6/2007 | Berner et al. |
| 2007/0197885 A1 | 8/2007 | Mah et al. |
| 2007/0264721 A1 | 11/2007 | Buck |
| 2007/0272746 A1* | 11/2007 | Ortiz et al. ................. 235/385 |
| 2008/0039702 A1 | 2/2008 | Hayter et al. |
| 2008/0056946 A1 | 3/2008 | Ahmad |
| 2008/0081977 A1 | 4/2008 | Hayter et al. |
| 2008/0098802 A1 | 5/2008 | Burke et al. |
| 2008/0101988 A1 | 5/2008 | Kang et al. |
| 2008/0121045 A1 | 5/2008 | Cole et al. |
| 2008/0153350 A1* | 6/2008 | Dei Rossi et al. ............. 439/607 |
| 2008/0161666 A1 | 7/2008 | Feldman et al. |
| 2008/0173552 A1 | 7/2008 | Wu et al. |
| 2008/0249385 A1 | 10/2008 | Phan |
| 2008/0255434 A1 | 10/2008 | Hayter et al. |
| 2008/0255437 A1 | 10/2008 | Hayter |
| 2008/0255808 A1 | 10/2008 | Hayter |
| 2008/0256048 A1 | 10/2008 | Hayter |
| 2008/0278331 A1 | 11/2008 | Hayter et al. |
| 2008/0288180 A1 | 11/2008 | Hayter et al. |
| 2008/0288204 A1 | 11/2008 | Hayter et al. |
| 2008/0300919 A1 | 12/2008 | Charlton et al. |
| 2008/0300920 A1 | 12/2008 | Brown et al. |
| 2008/0301158 A1 | 12/2008 | Brown et al. |
| 2009/0023222 A1 | 1/2009 | Wu et al. |
| 2009/0030641 A1 | 1/2009 | Fjield et al. |
| 2009/0098657 A1 | 4/2009 | Blais et al. |
| 2009/0118604 A1 | 5/2009 | Phan et al. |
| 2009/0130874 A1* | 5/2009 | Englund ................. 439/131 |
| 2009/0146826 A1 | 6/2009 | Gofman et al. |
| 2009/0213360 A1 | 8/2009 | Braig et al. |
| 2009/0305319 A1 | 12/2009 | Baudenbacher et al. |
| 2009/0325205 A1 | 12/2009 | Fujii et al. |
| 2010/0122074 A1* | 5/2010 | Drucker et al. ................. 713/1 |
| 2010/0159610 A1 | 6/2010 | Sun et al. |
| 2010/0268475 A1 | 10/2010 | Kusumoto |
| 2010/0309947 A1 | 12/2010 | Parasnis et al. |
| 2010/0319436 A1 | 12/2010 | Sun et al. |
| 2011/0191059 A1 | 8/2011 | Farrell et al. |

FOREIGN PATENT DOCUMENTS

| | | |
|---|---|---|
| EP | 1141684 | 2/2005 |
| EP | 1909097 | 4/2008 |
| GB | 2 102 569 | 2/1983 |
| WO | WO 99/32881 | 7/1999 |
| WO | WO 00/40953 | 7/2000 |
| WO | WO 03/032138 | 4/2003 |
| WO | WO 03/082098 | 10/2003 |
| WO | WO 2004/113896 | 12/2004 |
| WO | WO 2004/113912 | 12/2004 |
| WO | WO 2004/113913 | 12/2004 |
| WO | WO 2005/000114 | 1/2005 |
| WO | WO 2005/001462 | 1/2005 |
| WO | WO 2005/001680 | 1/2005 |
| WO | WO 2005/003748 | 1/2005 |
| WO | WO 2005/008231 | 1/2005 |
| WO | WO 2005/108968 | 11/2005 |
| WO | WO 2006/109279 | 10/2006 |
| WO | WO 2006/109453 | 10/2006 |
| WO | WO 2008/130896 | 10/2008 |
| WO | WO 2008/138553 | 11/2008 |
| WO | WO 2009/052222 | 4/2009 |
| WO | WO 2009/119116 A1 | 10/2009 |

OTHER PUBLICATIONS

Huang C. et al.; "Optical Temperature Measurement by Grating Expansion for Rotating Semiconductor Wafers", Journal of Vacuum Science and Technology: Part A AVS/AIP, Melville, NY, U.S. vol. 14, No. 2 (Mar. 1, 1996) pp. 271-277.

International Search Report mailed Jan. 2, 2009 issued during prosecution of corresponding International Patent Application No. PCT/US2008/080055, 2 pages.

International Written Opinion mailed Jan. 2, 2009 issued during prosecution of corresponding International Patent Application No. PCT/US2008/080055, 5 pages.

International Search Report mailed Feb. 22, 2010, issued during prosecution of corresponding International Patent Application No. PCT/US2009/060862, 5 pages.

International Written Opinion mailed Feb. 22, 2010, issued during prosecution of corresponding International Patent Application No. PCT/US2009/060862, 7 pages.

International Search Report mailed Mar. 5, 2010 issued during prosecution of corresponding International Patent Application No. PCT/US2009/059430, 6 pages.

International Written Opinion mailed Mar. 5, 2010 issued during prosecution of corresponding International Patent Application No. PCT/US2009/059430, 12 pages.

International Search Report mailed Oct. 5, 2010 issued during prosecution of corresponding International Patent Application No. PCT/US2010/039664; 7 pages.

International Written Opinion mailed Oct. 5, 2010 issued during prosecution of corresponding International Patent Application No. PCT/US2010/039664; 8 pages.

International Search Report mailed Oct. 29, 2010 issued during prosecution of corresponding International Patent Application No. PCT/US2010/037761, 4 pages.

International Written Opinion mailed Oct. 29, 2010 issued during prosecution of corresponding International Patent Application No. PCT/US2010/037761, 5 pages.

Extended European Search Report mailed Mar. 18, 2011 issued during prosecution of corresponding European Patent Application No. 08840230.0 (9 pages).

* cited by examiner

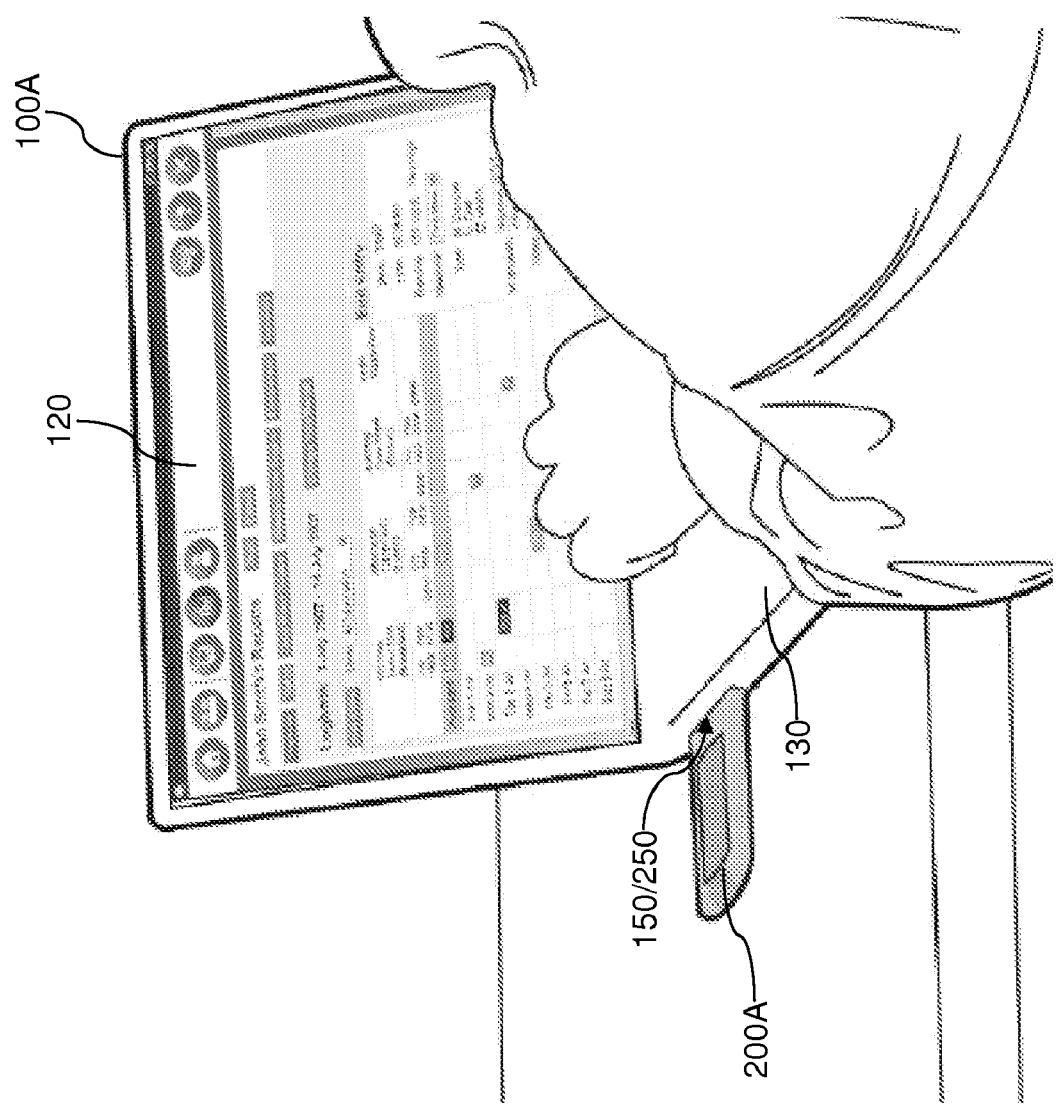

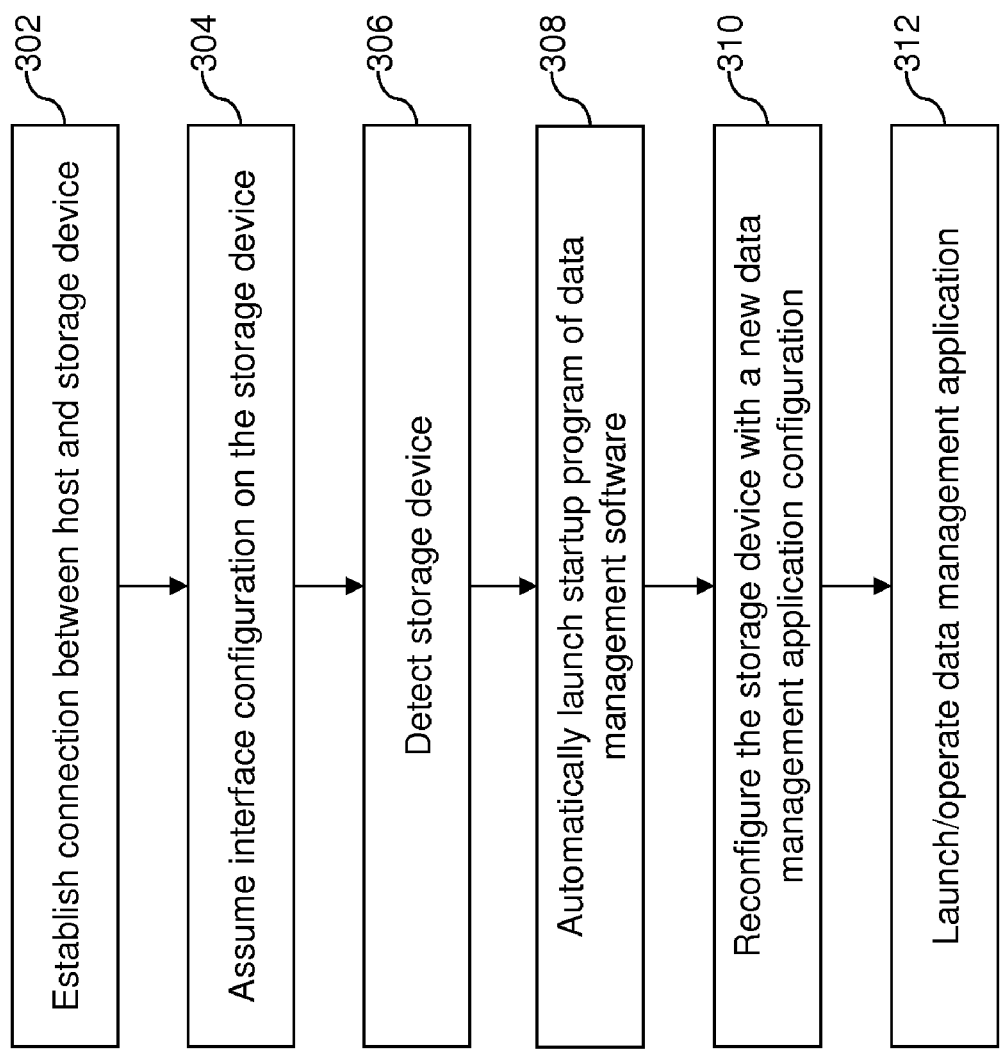

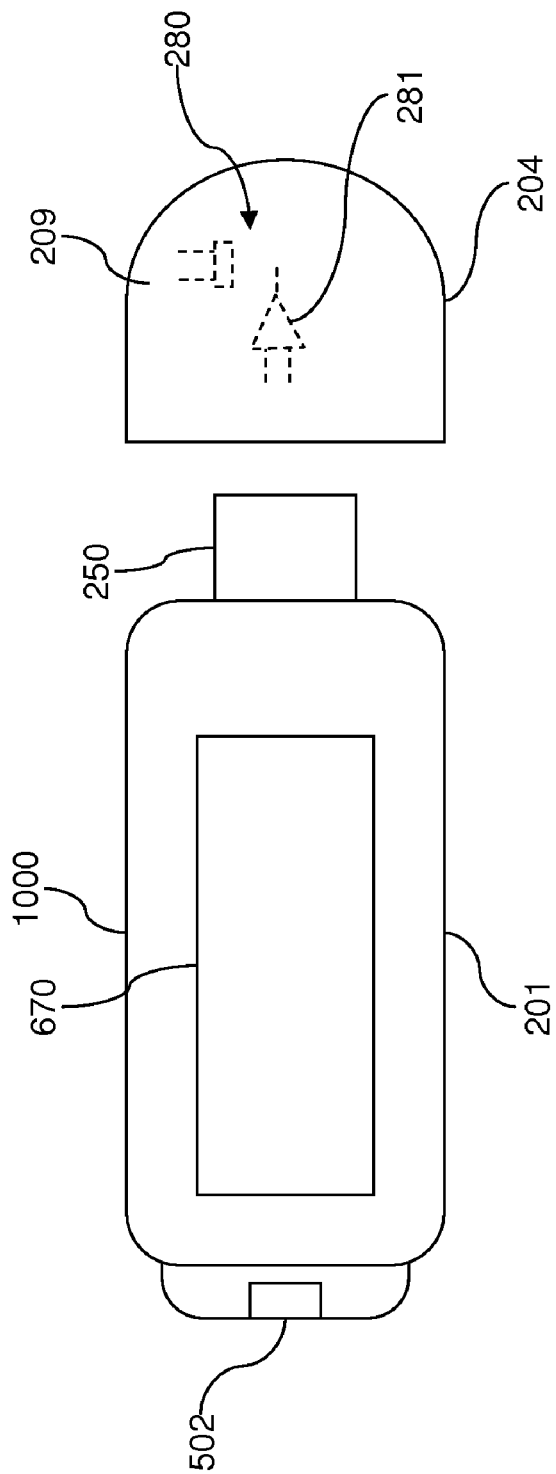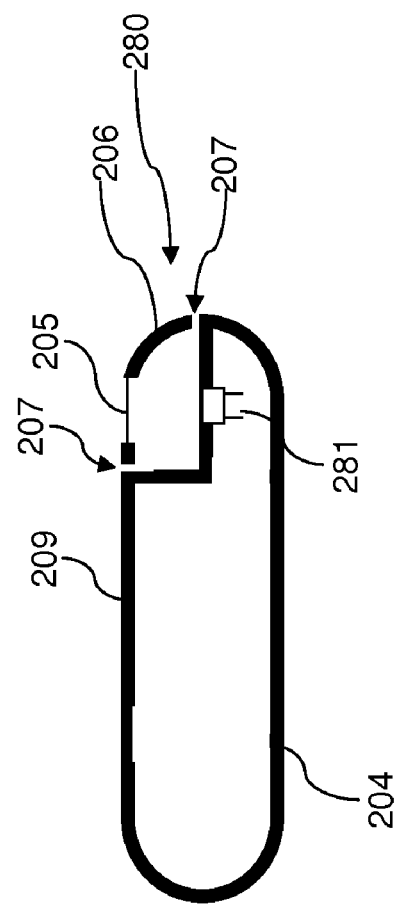
FIG. 10A
FIG. 10B

HEALTH DATA MANAGEMENT DEVICE

CROSS REFERENCE TO RELATED APPLICATIONS

This application claims priority to U.S. Provisional Application No. 60/932,286, filed May 30, 2007, U.S. Provisional Application No. 61/012,721, filed Dec. 10, 2007, and U.S. Provisional No. 61/012,718, filed Dec. 10, 2007, the contents of which are incorporated entirely herein by reference.

FIELD OF THE INVENTION

The present invention relates generally to a method and system for managing health data. More specifically, the present invention relates to a portable system that securely manages and displays information associated with the health of an individual, such as measurements of glucose in a blood sample.

BACKGROUND OF THE INVENTION

The quantitative determination of analytes in body fluids is of great importance in the diagnoses and maintenance of certain physiological conditions. For example, individuals with diabetes frequently check the glucose level in their bodily fluids. The results of such tests can be used to regulate the glucose intake in their diets and/or to determine whether insulin or other medication needs to be administered.

Diagnostic systems, such as blood-glucose systems, may employ an instrument, such as a meter, to calculate the glucose value in a fluid sample from an individual. Such instruments operate by measuring an output, such as current or light, from a reaction with the glucose in the sample. The test results typically are displayed and stored by the meter. Basic systems allow the user to access the test results directly from the meter via a keypad or other interactive component.

SUMMARY OF THE INVENTION

A portable data-management system is provided for securely managing and displaying information associated with the health of an individual, such as measurements of glucose in a blood sample.

An embodiment provides a device for managing health data, comprising: a first housing portion including a data storage system that stores health data; and a second housing portion including a data communications element that provides data communications between the data storage system and a processing device by connecting with the processing device, the processing device processing the health data according to a data-management software, wherein the first housing portion and the second housing portion are connected by a cable that communicates signals between the data communications element and other components in the first housing portion.

A further embodiment provides a device for managing health data, comprising: a first housing portion including a health data management system and a data communications element that provides data communications between the health data management system and an external processing device; and a second housing portion that is removably coupled to the first housing portion, the second housing portion including at least one component used by the health data management system.

Still other aspects, features, and advantages of the present invention are readily apparent from the following detailed description, by illustrating a number of exemplary embodiments and implementations, including the best mode contemplated for carrying out the present invention. The present invention is also capable of other and different embodiments, and its several details can be modified in various respects, all without departing from the spirit and scope of the present invention. Accordingly, the drawings and descriptions are to be regarded as illustrative in nature, and not as restrictive. The invention is to cover all modifications, equivalents, and alternatives falling within the spirit and scope of the invention.

BRIEF DESCRIPTION OF THE DRAWINGS

FIG. 1B illustrates an example of the data-management system of FIG. 1A.

FIG. 2 illustrates a flowchart for launching a data-management application from a portable device.

FIG. 10A illustrates a view of a portable device with a temperature sensor stored in an end cap.

FIG. 10B illustrates a view of a temperature sensor that may be employed in the end cap of FIG. 10A.

DESCRIPTION OF ILLUSTRATED EMBODIMENTS

A portable data-management system is provided for securely managing and displaying information associated with the health of an individual, such as measurements of glucose in a blood sample. The data-management system is advantageous to individuals who are actively involved in monitoring and recording measurements of their blood glucose concentrations and/or other analytes or fluids of interest. Individuals who test frequently can more easily manage their test results as well as other health data with the data-management system. The data-management system may be employed with different processing devices at varying locations, as there is essentially no need to pre-install additional programs, agents, device drivers, or other software components on the separate processing devices to operate the data-management system. A portable device stores software for a data-management application that receives and processes test results and other health data. The portable device may employ an interface protocol that is compatible with the operating systems and hardware configurations of different types of processing devices. Once the portable device is connected to a processing device, the data-management application may be launched on the processing device.

The data-management system also may integrate advanced data processing and display features with the portable device. As such, the users may access some advanced presentations of health data without launching the data-management application on a separate processing device. In addition, the data-management system may integrate other functions, such as an analyte measurement function, with the portable device.

Due to the portability of the data-management system, the data-management system also addresses issues related to the security of data, such as personal medical information. The data-management system ensures that all data is stored on the portable device in the user's possession and that no data is transferred to and stored by other processing devices. Thus, a user may use a public computer to interface with the portable device and no data will remain on the public computer for others to view. Other security functionality, such as user-authentication procedures, may also be implemented to enhance security data. Furthermore, the data-management system may also preserve data integrity during the transfer of data between the portable device and other devices.

Figure 1A:
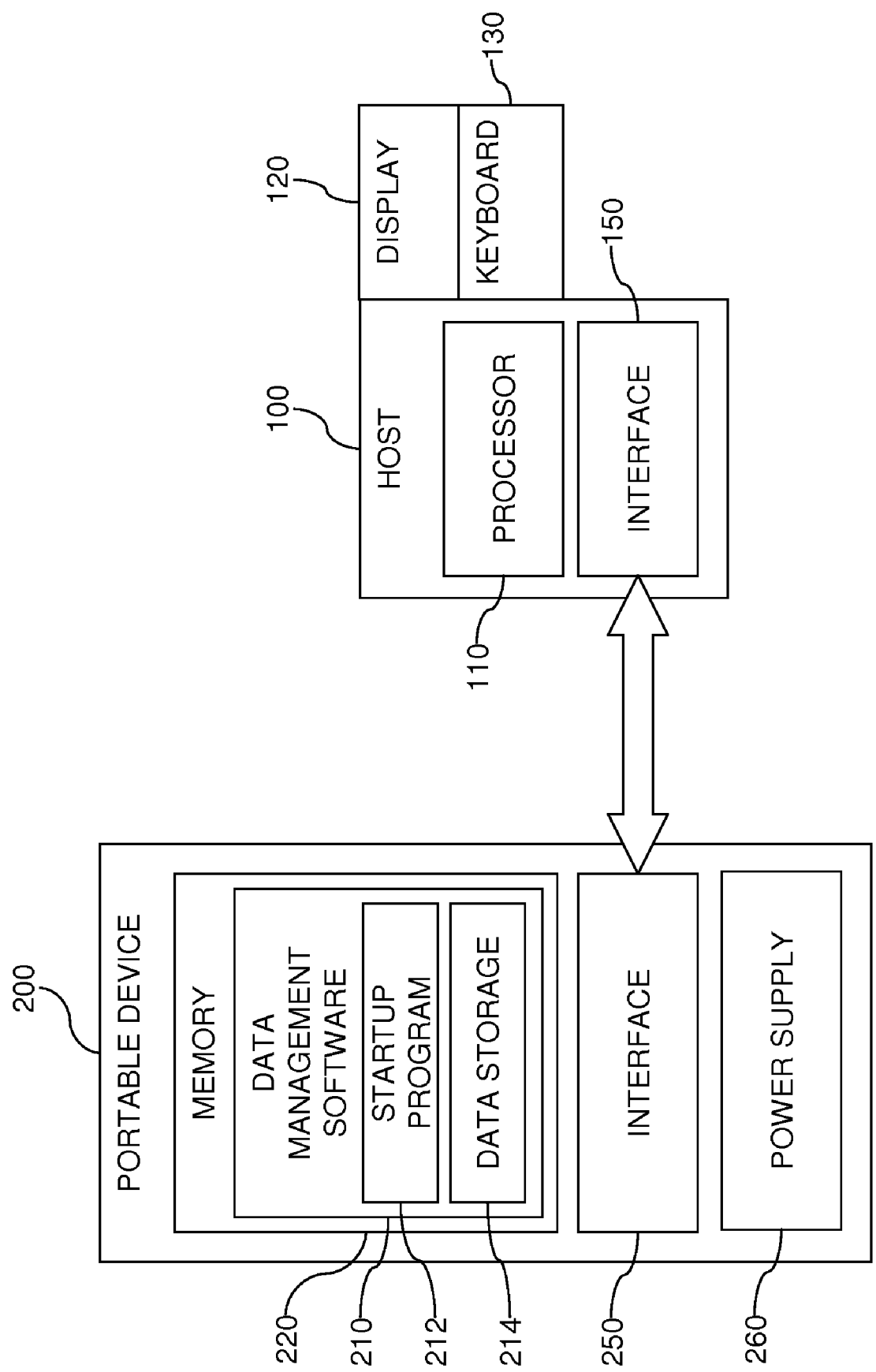
FIG. 1A illustrates a data-management system including a portable device connected to a processing device.

FIG. 1A illustrates a data-management system 10 including a processing device 100 and a portable device 200. The processing device 100 may be a desktop or laptop personal computer (PC), a handheld or pocket personal computer (HPC), a compatible personal digital assistant (PDA), a smart cellular phone, or the like. In addition, the processing device 100 may employ any operating system and configuration. If the processing device 100 is a desktop or laptop personal computer, the operating system may be a version of Microsoft® Windows®. Alternatively, if the processing device 100 is a PDA, the operating system may correspond with those of PALM® handhelds from Palm, Inc., or Blackberry® devices from Research in Motion Limited. In general, the processing device 100 includes a processor 110 that is capable of receiving and executing any number of programmed instructions. In addition, the processing device 100 is typically operated with a display 120 and a keyboard 130, and/or other input/output elements, which may be external to, or integrated with, other components of the processing device 100.

As described in greater detail below, the portable device 200 may be employed in combination with hosts that can execute tasks but that are not full-function processing devices. Such hosts may include task specific devices such as printers, display devices, fluid analyte meters (e.g., blood glucose meters), or the like. In general, while a particular configuration of the data-management system may be described, other configurations may be used including those employing other hosts, storage devices, and additional components.

Figure 1D:
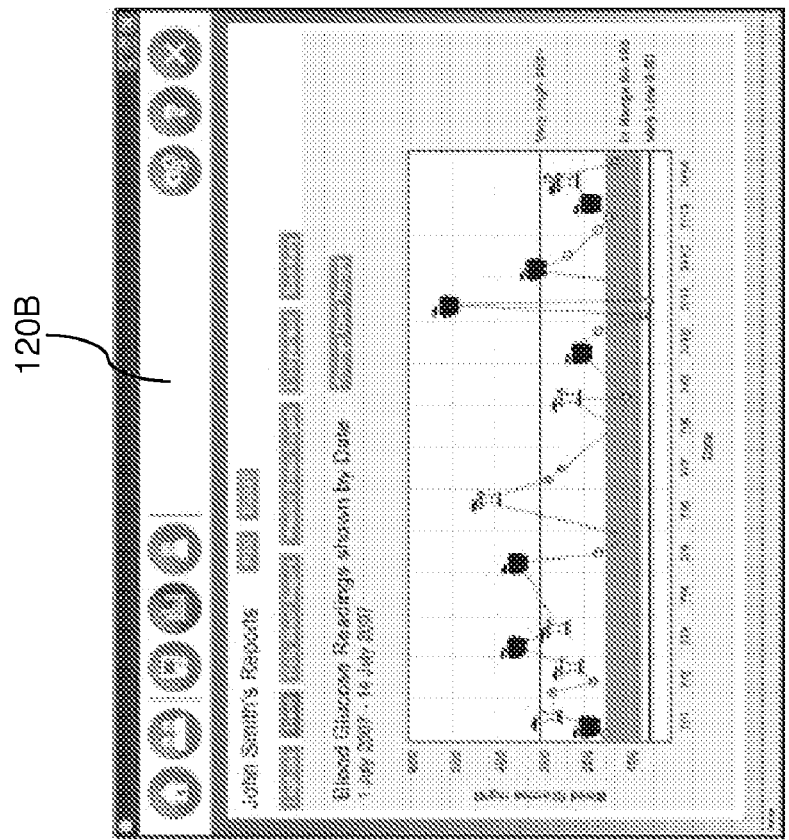
FIG. 1D illustrates another example of a display for the data-management system of FIG. 1A.
Figure 1C:
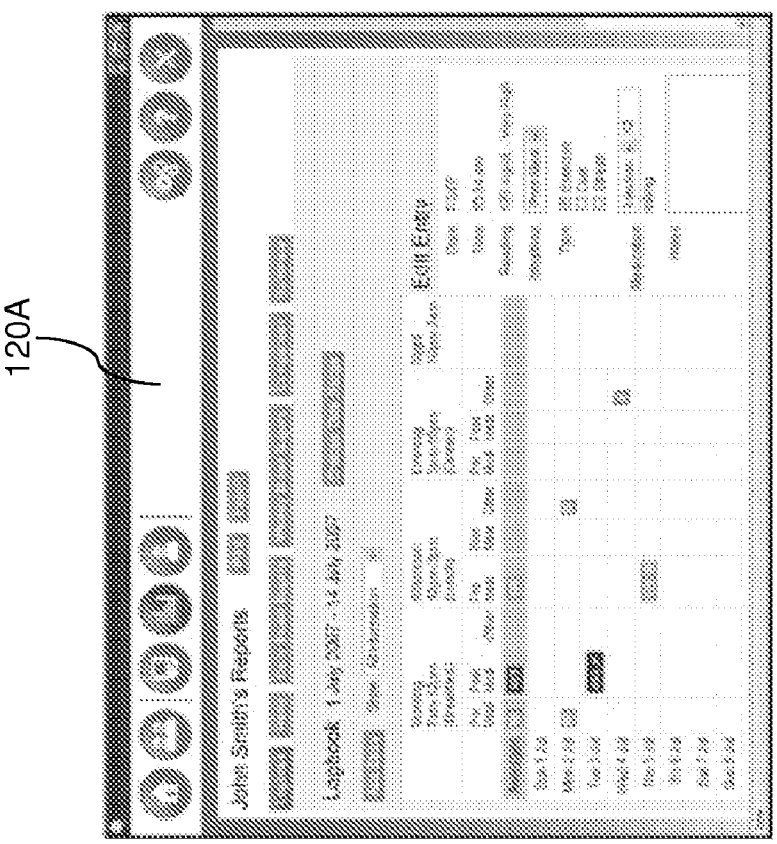
FIG. 1C illustrates an example of a display for the data-management system of FIG. 1A.

The portable device 200 may be sized to be easily carried, transported, and stored by an individual. The portable device 200 may include a memory, or data storage, 220, such as flash memory, Electrically Erasable Programmable Read-Only Memory (EEPROM), or the like. The memory 220 may be configured to include a combination of storage technologies. The memory 220 stores data-management software 210 associated with the data-management system 10. The data-management software 210 may be a collection of programs or computer code that receives and processes measured data and/or other input. The data-management software 210 processes and/or displays this input in a manner that is desired or selected by the user or other individuals. This information may be used by a user, home care provider (HCP), a physician, and/or other individuals. As discussed previously, the measured data may include information from the testing of an analyte including the concentration of glucose and/or other analytes in a person's blood or other fluid. The software 210 can provide the advanced displays and data processing that may be required by a user who tests multiple times a day (e.g., from about six to about ten times a day). For example, the software 210 may include a product similar to WINGLUCO-FACTS® Diabetes Management Software available from Bayer HealthCare LLC (Tarrytown, N.Y.). As such, the software 210 may provide a complete tool kit that receives and stores test results from a blood glucose-measurement system, receives and stores other testing information, such as test times and meal markers, tracks test results in an electronic logbook, calculates averages and provides other statistical analysis, summarizes and provides feedback on the test results, provides a customizable graphical user interface, displays user-friendly charts and graphs of the test results, tracks test results against user-specific target ranges, provides predictive analysis, and/or sends data to healthcare professionals via fax, email, or the like. FIG. 1C illustrates an exemplary display 120A presenting test results from a blood glucose-measurement system in an electronic logbook format, while FIG. 1D illustrates an exemplary display 120B presenting similar data as a graphical trend analysis. The memory 220 may also include other software in addition to the software 210.

The data-management system 10 is not limited to receiving and managing information from the testing of an analyte, such as blood glucose. Indeed, the data-management system 10 may receive data from other systems or devices that measure and/or record health data and do not require analyte testing, such as body-temperature measurements, blood-pressure measurements, heart rate measurements, blood-oxygen content measurements, breathing measurements for chronic obstructive pulmonary disease (COPD) analysis, weight measurements for analyzing Lasix use, or the like.

The data-management software 210 may include a combination of software programs or components. In FIG. 1A, the data-management software 210 includes a startup or initialization program 212 that initiates the data-management application. The startup program 212 can identify the relevant capabilities and platform of the processing device 100 so that a platform-compatible application may be selected and launched for execution on the processing device 100. As such, the software 210 may be compatible with one or more platforms/operating systems. Greater compatibility of the software 210 enhances the portability of the data-management system 10.

In addition, the software 210 may employ data storage 214, such as an embedded database, for receiving and storing test results. The data-management system 10 addresses issues related to the security of data, such as personal medical information, by ensuring: (1) essentially all data is stored and processed on the portable device 200, which remains in the user's possession; and (2) no readable data is permanently transferred from the data storage 214 to the processing device 100, which other individuals may access. Thus, a user may use a public computer to interface with the data-management system 10 and no data remains on the public computer for others to view. Although the data-management system 10 may temporarily transfer data to RAM or other similar storage on the processing device 100, a cleanup or termination procedure in the software 210 ensures that any such transferred data is removed from the processing device 100 when execution of the software 210 is terminated. However, as described further below, the software 210 may be executed directly from the portable device 200, so that no memory, e.g. RAM, on the processing device 100 is used to hold any data even temporarily.

If a particular processing device 100 is trusted by a user and/or is frequently employed by the user, the user may register the processing device 100 with the portable device 200 to allow data transfer to the processing device 100. A unique device identifier for the processing device 100 may be recorded on the portable device 200, so that the portable device 200 can recognize the processing device 100 and permit data transfer to the processing device 100.

Data security may also be enhanced by employing the data storage 214 (e.g., an embedded database) that can only be accessed or decrypted by the data-management software 210. Furthermore, the software 210 may also include programs or components, such as user-authentication routines, that protect data integrity and security. When the data-management software 210 launches, it may immediately prompt the user for a user ID and password, personal identification number (PIN), and/or other authentication information. The user is only allowed access to data on the portable device 200 if the response to the security prompt corresponds with authentication information stored with the data-management system 10. A user-authentication routine may also be employed to permit data to be transferred from the portable device 200 to the processing device 100.

In addition, a memory map may be employed where the memory 220 is configured to have multiple security levels. In other words, areas of the memory 220 are designated for different levels of access and manipulation, e.g., some areas may be more restricted than others. For example, a first layer may permit open access for data writes, deletes, and changes, while a second layer may be completely unchangeable. As such, a software kernel, core programs, critical permanent data, and the like may be stored on the second layer to protect the software and the data from corruption or deletion.

As discussed previously, the memory 220 may be configured to include a combination of storage technologies. Accordingly, the software kernel, the data-management software 210, and the like may be stored on an EEPROM or other primary device. The data-management software 210 is launched on the processing device 100 from the EEPROM. Meanwhile, data processed by the data-management software 210 is stored on a separate flash memory or other memory device on the portable device 200.

As discussed previously, the portable device 200 may include a flash memory device, such as a universal serial bus (USB) flash drive or a memory card. USB flash drives are also known as thumb drives, handy drives, flash sticks, or jump drives. Memory cards may have a variety of formats, including PC Card (PCMCIA), CompactFlash (CF), SmartMedia (SM/SMC), Memory Stick (MS), Multimedia Card (MMC), Secure Digital Card (SD), xD-Picture Card (xD), Intelligent Stick (iStick), ExpressCard, some variation thereof, or the like. Flash memory devices may employ non-volatile memory so that the software associated with the data-management software 210 may be retained in the portable device 200 even when the portable device 200 receives no power. The portable device 200 may employ other storage media, such as floppy disk or optical disc (CD, DVD, Blu-ray disc).

In some embodiments, the memory 220 in the portable device 200 may include execute-in-place (XIP) memory, such as NOR (NOR digital logic gate) flash memory, so that the data-management software 210 stored on the memory 220 can be executed directly without the need to copy them into RAM on the processing device 100. Accordingly, the data-management system 10 can secure the data by ensuring that essentially all data is stored and processed by a data-management system 10 running off a portable device in the user's possession and that essentially no data is transferred to other processing devices. Thus, a user may use a public computer to interface with the system and no data will remain on the public computer for others to view.

The portable device 200 may interface with the processing device 100 in a convenient plug-n-play (PnP) approach. The interface enables data communications between the portable device 200 and any processing device 100 and permits the data-management software 210 to be used with the processing device 100. In particular, the portable device 200 has an interface element 250 that is compatible with an interface element 150 on the processing device 100. The portable-device interface element 250 may physically engage the processing-device interface element 150 to form a hardware interface. In other words, a physical or wired connection between the processing device 100 and the portable device 200 may be employed. FIG. 1B illustrates a portable device 200A physically connected, e.g., plugged in, via interface elements 150/250 to a processing device 100A, which is a laptop PC with a display screen 120 and a keyboard 130. The portable device 200 may be a USB flash drive, and the processing-device interface element 250 may be a USB connector that is received into a USB port, which acts as the processing-device interface element 150 on the processing device 100. Thus, the portable device 200 employs a USB mass-portable device (USB MSD) configuration that enables communication between the processing device 100 and the portable device 200 according to a set of standard computing communications protocols. The USB connector on the portable device 200 is easily inserted into and removed from the USB port on the processing device 100. In addition, adapters may be required to enable connection, for example, between the portable device 200 and a processing device 100 employing mini-USB, micro-USB, or the like. While FIG. 1A shows a single interface element 250, the portable device 200 may include more than one interface element 250 to enable connections according to more than one interface technology.

USB ports appear on most conventional desktop and laptop PCs, for example, and the USB mass storage standard is supported natively by modern operating systems such as Microsoft® Windows®, Mac OS®, Linux, and other Unix-like systems. As USB communications are natively supported by a wide variety of devices, additional programs, agents, device drivers, or other software components do not have to be installed locally on the processing device 100 to enable communication with the mass-portable device (USB MSD) configuration of the portable device 200.

The portable device 200 also may be a Secure Digital (SD) memory card with a series of contacts that act as the interface element 250. The processing-device interface element 150 may be an expansion slot that receives the contacts of the memory card. The processing device 100 and the portable device 200 may comply with SDIO (Secure Digital Input Output) interface specifications. Other memory card formats having different interface specifications may be employed. However, having an SDIO is advantageous because many processing devices such as PDAs, HPCs and smart cellular phones include an expansion slot that is SDIO compatible.

Additionally or alternatively, the interface elements 150 and 250 also may enable the processing device 100 and the portable device 200 to communicate via a radio-frequency (RF) link (e.g., a short-range RF telemetry), such as Bluetooth® wireless technologies, Zigbee, Z-Sense™ technology, FitSense, BodyLAN™ system, and other RF technologies. RF technologies such as Bluetooth® enable external devices to communicate wirelessly with, for example, laptop personal computers and mobile phones. Other wireless, or non-physical, communication technologies, such as infrared (IR) links, also may be used.

Preferably, the storage service 200 employs an interface element 250 that is compatible with at least one interface technology, or protocol, such as USB, SD, or Bluetooth® technology. If a widely-used interface technology is used, the processing device 100 is more likely to provide native support for the interface with the storage service 200. In this way, the data-management software 210 on the portable device 200 may be immediately executed on different types of processing devices 100 having varying operating systems and hardware configurations, making the data-management system 10 more portable.

The flowchart of FIG. 2 illustrates how the data-management software 210 on the portable device 200 may be implemented on the processing device 100. In act 302, the processing device 100 is initially connected to the portable device 200. As discussed previously, the processing-device interface element 150 and the portable-device interface element 250 may establish this connection according to an interface technology. For example, the user may insert a USB connector on the portable device 200 into a USB port on the processing device 100.

As also discussed previously, the processing device 100 may provide native support for the interface technology employed by the portable device 200. Thus, the processing device 100 can immediately communicate, in act 304, according to the existing configuration of the portable device 200. If the portable device 200 employs a USB MSD configuration and the processing device 100 supports this configuration, communication is established automatically between the processing device 100 and the portable device 200. Due to the wide use of USB interfaces, additional programs, agents, device drivers, or other software components do not generally have to be pre-installed on the processing device 100 to make the processing device 100 compatible with the USB MSD configuration on the portable device 200.

In act 306, the processing device 100 detects the portable device 200. In FIG. 1A, the data-management software 210 includes the startup program 212. In act 308, the startup program 212 may be launched once the processing device 100 detects the portable device 200. The startup program 212 may be launched automatically or upon input from the user, another person, or another component. Many operating systems provide an auto-launch feature that allows the system to take some action immediately upon the insertion of removable media, such as a CD-ROM, DVD-ROM, or flash media. The processing device 100 may employ a version of the Microsoft® Windows® operating system that provides the AutoRun, or AutoPlay, feature that automatically launches the startup program 212. For some processing devices 100, such as those that employ the Microsoft® Windows® operating system, the portable device 200 may first have to announce to the processing device 100 that it is a non-removable device before the auto-launch feature of the operating system is triggered to run the startup program 212.

In act 310, the startup program 212 reconfigures the portable device 200 from the initial USB MSD configuration to a new configuration specific to the data-management software 210. The new data-management configuration allows the data-management application to be launched and operated in combination with the processing device 100, in act 312. The data-management configuration also supports related functions such as managing updates to the data storage 214.

Reconfiguring the portable device 200 from the more universal USB MSD configuration to the specific data-management configuration can prevent or inhibit other applications on the processing device 100 from accessing the files and data on the portable device 200, thereby making the data-management system 10 more secure. If the processing device 100 employs the Microsoft® Windows® operating system, the Windows® Explorer program, which provides a graphical user interface for accessing the file systems, is unable to access the files on the portable device 200 when the portable device 200 has been reconfigured specifically for the data-management application. This reconfiguration may occur automatically upon connection between the portable device 200 and the processing device 100, thereby preventing non-designated applications on the processing device 100 from accessing any data on the portable device 200.

Due to the plug-n-play aspects of the interface between the processing device 100 and the portable device 200, the processing device 100 and the portable device 200 may be connected or disconnected by the user at any time. As such, the data-management system 10 also ensures that the data or software on the portable device 200 is not corrupted when the portable device 200 is connected or disconnected from the processing device 100. Checksum and/or data commit routines may be employed to ensure that data is successfully transferred and stored, thus promoting the preservation of data integrity. In addition, as discussed previously, when the portable device 200 is disconnected, the data-management software 210 may perform a clean-up or termination procedure to remove any data stored temporarily on the processing device 100, e.g., RAM, and exits gracefully.

Although the portable device 200 and the data-management software 210 stored thereon may be compatible with a variety of processing devices 100 having different operating systems, the data-management system 10 may also employ another processing device 100 that acts as a base-station. The portable device 200 may connect with the base-station processing device using the interface technologies described herein. The base-station processing device may provide a repository for longer term storage of data downloaded from the portable device 200. In addition, a master version of the data-management application may be launched from the portable device 200 with the base-station processing device. For example, the base-station processing device may be an individual's home PC.

In addition, the portable device 200 may be provided with an expansion port that can receive additional devices, such as an SD memory card. The interface at this expansion port operates similarly to the other interfaces described herein. In particular, the interface may employ an SDIO interface to accept an SD card. The additional memory on the SD card can be used to store a larger database for test results.

In addition to storing data, such as test results from a blood glucose-measurement system and other health data processed by the data-management software 210, the portable device 200 may be employed to incorporate the function of a portable medical records device, due to its portability and compatibility. As such, the portable device 200 may be used to facilitate the sharing of important information with emergency medical technicians (EMT's), doctors, other health care providers, or the like.

In a particular embodiment, the portable device 200 may provide important information during emergency situations. If the user is unconscious or otherwise unable to communicate with a care giver, the care giver may connect the portable device 200 with a processing device 100 via interface element 250 and once the data-management software 210 is launched, important information may appear on a splash screen or initial screen. This type of functionality is possible, because the portable device 200 is highly compatible with a variety of processing devices 100, and the care giver does not have to pre-install software components on the processing device 100 to launch the software 210.

In some cases, the data-management system software 210 may be distributed to the health care community, so that data on the portable device 200 may be accessed, if authorized, with the data-management system software 210 installed on the health care provider's processing device 100, e.g. PC. For security purposes, data may be encrypted so that it may only be read with a decryption key on the health provider processing device. If an instance of the software 210 is already running on the processing device 100, the software 210 on the portable device 200 may be prevented from launching so that two instances of the software 210 are not running. As the portable device 200 and processing device 100 may have different versions of the data-management system software 210, a procedure may be required to reconcile the different versions. Different versions of the software may organize and store data differently and/or collect different types of data. In other words, the structure of the data storage 214 and the types of data stored therein may depend on the version of software 210. For example, if the health care provider's processing device has a newer version of the software 210, the newer version may be developed to be backward compatible with older versions of the software 210 and can operate on the data on the portable device 200. If, however, the health care provider's processing device 100 has an older version of the software 210, the older version 210 may terminate and the newer version on the portable device 200 may be launched on the health care provider's processing device 100. Other techniques for reconciling different versions may be employed. For example, the software 210 may be developed to provide a base set of functions that always operate the same way and to structure certain basic types of data, e.g., fluid analyte measurements, in the same way, so that at least some aspects of the software 210 are unchanging and thus forward and backward compatible.

In general, the types of data that can be stored and shared with other individuals, such as health care providers, include, but are not limited to: name and address information; data tracked for a disease state (logbook information, daily tracking for chronic illnesses and measurable markers, measurements collected over the last 12 hours, etc.); comorbidity data; last dose of insulin or other medication taken; primary doctor's name and contact information; information on past visits to a doctor; a living will; information on a health care proxy; insurance information; allergy information; and other user-provided information. Alternatively or additionally, information can be provided on a sticker or other label affixed to the portable device 200.

To preserve the user's privacy, information shared through the portable device 200 is strictly controlled by the user. As a further technique for controlling shared data, the data-management software 210 may provide multiple levels of access so that certain types of data are only accessible to certain individuals/organizations. For example, an EMT may only be able to access information such as doctor's information and data generally available on a medical bracelet. In other words, the software provides very basic functionality, e.g., displaying a single splash screen, to present less sensitive personal information to those without higher authority. Meanwhile, a doctor may be able to access more sensitive health-related information. Furthermore, greater access may be provided to relatives or close care givers, e.g., parents of a child with diabetes.

As described previously, the portable device 200 may include a variety of interfaces 250 to connect and communicate with a variety of devices. In addition to connecting with a processing device 100 to launch data-management software 210 as described previously, the portable device 200 may employ its communication capabilities to connect remotely, e.g., over a network, with external systems to provide the user with a wider range of functionalities and features. In some embodiments, these external systems may provide a host function that manages the communication between the portable device 200 and these external systems. These external systems may execute aspects of the data-management software 210 or other software components stored on the portable device 200 to enable the communication between the portable device 200 and the external systems. Alternatively, these external systems may store the necessary software components locally.

Accordingly, the portable device 200 may connect to an intermediate device, such as a PC with access to the Internet or a mobile communications device with access to a cellular network, to transmit data remotely to other individuals, e.g., health care providers. As such, a user does not have to connect the portable device 200 directly with the other individual's processing device 100 to share data. The health data stored on a portable device 200 is therefore easily shared with other individuals, including health care specialists who may be located in distant or remote locations. This feature may be particularly advantageous for users unable to a health care provider's facilities due to health problems, distance, cost, etc. Moreover, this feature enhances the health care provider's ability to monitor a user's health data with greater frequency and immediacy. The transmission of the data may be managed by the intermediate device, which may include a processor to execute the appropriate software components stored on the intermediate device or on the portable device 200.

In addition, the portable device 200 may connect to an intermediate device to receive field upgrades to the data and/or software stored on the portable device 200. For example, the portable device 200 may conveniently receive an updated/patched version, or even a completely new version, of the data-management software 210 by connecting to a remote download server through a networked PC or a mobile communications device. As a further example, the portable device 200 may receive new or updated parameters for the execution of software on the portable device 200. In some embodiments, new programs or features for the data-management system 10 may be received, e.g., purchased, from a remote download server. Optional features that may customize or personalize the graphical user interface for the data-management application may be available through a system accessible through the Internet. To maintain the integrity of the data and software on the portable device 200, data or software downloaded via field upgrade may be validated before being employed in the portable device 200. For example, checksum routines may be employed to confirm that data or software has been successfully downloaded in its entirety. The field upgrade may be managed by the intermediate device, which may include a processor to execute the appropriate software components stored on the intermediate device or on the portable device 200. Additionally or alternatively, the portable device 200 may include a processor that can locally execute software components to manage aspects of the field upgrade. For example, the processor on portable device 200 may preserve data integrity on the portable device 200 according to a data update file (DUF) or other component that ensures that the software has been successfully downloaded. For additional data security, the DUF be employed with data encryption/decryption.

As discussed previously, embodiments of the portable device 200 may employ a USB interface to connect to a variety of devices. In conventional systems, standard USB is designed to provide connectivity between a processing device and peripheral devices, where the processing device acts as a host and the USB-enabled peripheral devices act as slaves. In general, with standard USB, only the USB host can initiate data transfers to the connected USB peripheral device, and the USB peripheral device can only respond to instructions given by the host. Thus, a USB-enabled peripheral device is not able to connect with other USB-enabled peripheral devices over a peer-to-peer communication channel. In FIG. 1B, where the processing device 100 is a laptop PC, one may consider the laptop PC to be a host and the portable device 200 to be a peripheral device. Once the software 210 is launched on the processing device 100, the processing device 100, via the software 210, may control the execution of program instructions and any data transfer with the portable device 200.

In other embodiments, however, the portable device 200 may include processing capabilities to act as a host. Therefore, the portable device 200 is not limited to the role of a slave as a peripheral device according to standard USB. In other words, the portable device 200 can communicate with a larger variety of devices via peer-to-peer communication, including devices that are conventionally considered to be peripheral devices.

For example, the portable device 200 may employ the USB 2.0 specification and USB On-The-Go (USB OTG), which is a supplement to the USB 2.0 specification. The USB OTG functionality enables the portable device 200 to communicate with other devices employing USB OTG. When two devices with USB OTG functionality connect with each other directly, a Host Negotiation Protocol (NHP) enables either one of the two devices to be a host. The NHP also enables the two devices to exchange host/slave roles. When a physical connection between two devices with USB OTG is established, one of the devices assumes the role of the host and powers up the USB $V_{BUS}$ with 8 mA current, so that USB data communication is realized between the two connected devices. A Session Request Protocol (SRP) may be used to prompt the host to turn on the USB $V_{BUS}$. The communication between the two devices is bi-directional or duplex, so data can be exchanged between the two devices. The communication can provide either low speed transfer (e.g., approximately 1.5 Mbits/sec), full speed transfer (e.g., approximately 12 Mbits/sec), or high speed transfer (e.g., approximately 480 Mbits/sec). Advantageously, USB OTG functionality is configured for use with battery-powered devices and tries to minimize power consumption. In this regard, the USB $V_{BUS}$ can be turned on and off by the host using the SRP.

It is also noted that if the portable device 200 in FIG. 1A includes USB OTG functionality and connects to a processing device 100 (without USB OTG), the processing device 100 and the portable device 200 can communicate via standard USB and the processing device 100 generally operates as the host as described previously. Other portable devices may employ communication protocols that provide advantages similar to those of USB OTG.

In an implementation of USB OTG, the portable device 200 may be connected directly with a USB-enabled printer and the data from the portable device 200 can be automatically printed. The portable device 200 may dynamically create ready-to-print or printable files and may send the files to a printer via the USB connection.

Device drivers and/or other software components may be required for the portable device 200 to interact with another device. For example, a printer driver may be required to print data that is uploaded to a printer. Thus, to print files, the portable device 200 may store and access the printer driver when the portable device 200 connects to the printer to print data. Because it may not be possible to install additional device drivers and/or other software components to the portable device 200 with USB OTG after the portable device 200 is manufactured, the portable device 200 may only be compatible with a preselected set of devices, where drivers for the set of devices were installed onto the portable device 200 during manufacturing. A list of compatible devices may be stored on the portable device 200, so that the portable device 200 can determine whether it is compatible with a given device.

In another example, a first portable device 200 with USB OTG can communicate directly with a second portable device 200, where one of the portable devices assumes responsibility as a host. As such, in one application, when a user wants to replace an old portable device with a new portable device, the data and configuration on the old portable device can be transferred easily and directly to the new portable device. In another application, the functionality available with the first portable device 200 may be shared with the second portable device 200, or vice versa. For example, the second portable device 200 may include interface elements that employ USB as well as an RF wireless protocol not available on the first portable device 200. However, if the first portable device 200 connects to the second portable device 200 via USB, the first portable device 200 may have access to the RF wireless protocol on the second portable device 200.

Data, such as test results from a blood glucose-measurement system, may be received by the data-management system 10 according to a variety of techniques. As the previous discussion of USB OTG indicates, the portable device 200 is not limited to interfacing with processing devices for launching software. Thus, in FIG. 3, the portable device 200 may connect directly with a measurement system 20 to enable data to be directly downloaded from the measurement system 20 onto the portable device 200.

Figure 3:
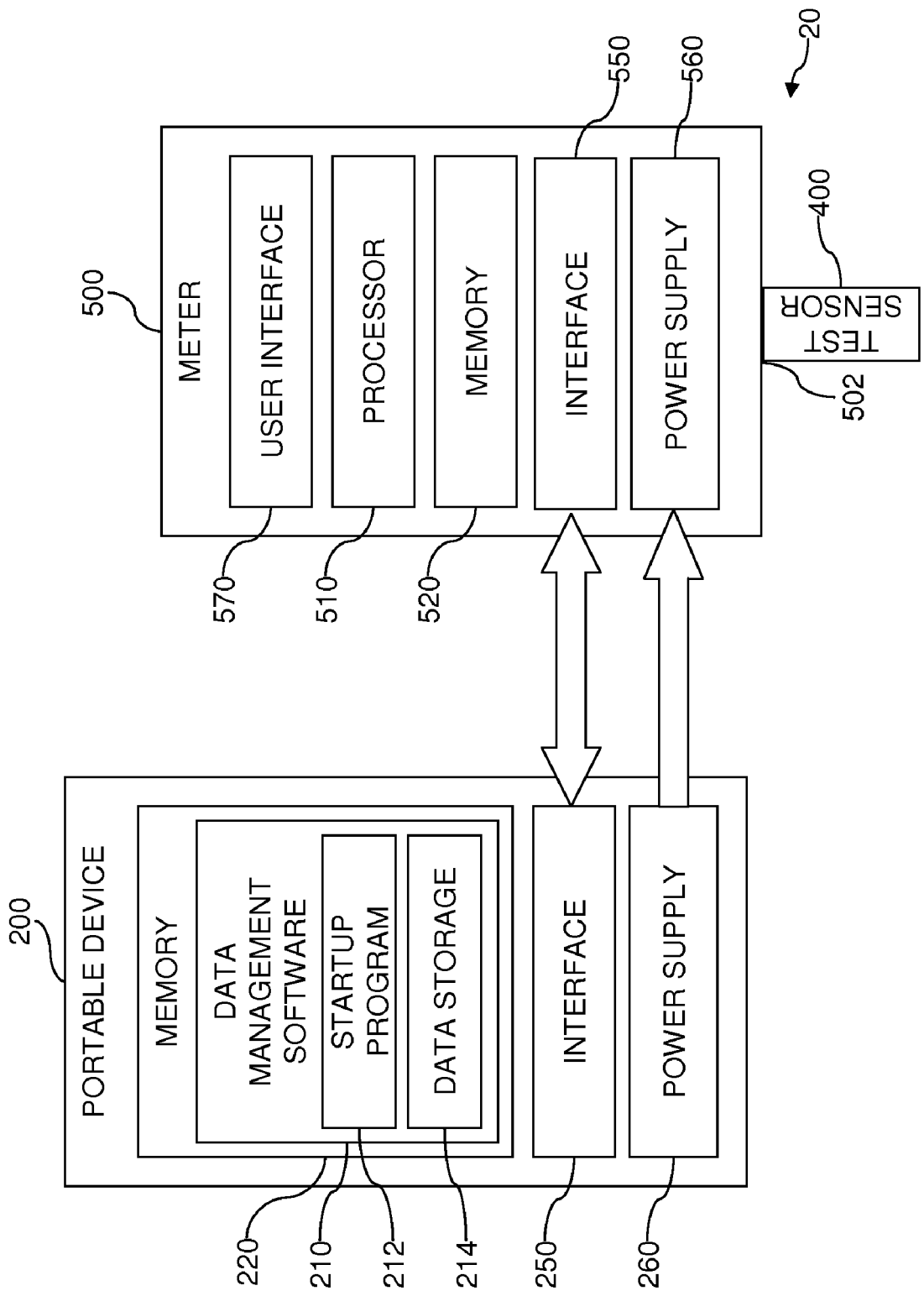
FIG. 3 illustrates a data-management system including a portable device connected to a measurement system.

FIG. 3 illustrates an exemplary measurement system 20 including a meter 500 with a port 502 for receiving and analyzing a fluid sample on a test sensor 400. The test sensor 400 is configured to receive a fluid sample that is analyzed using the meter 500. Analytes that may be analyzed include glucose, lipid profiles (e.g., cholesterol, triglycerides, LDL and HDL), microalbumin, hemoglobin $A_1C$, fructose, lactate, or bilirubin. Analyte information may, such as analyte concentrations, may be determined. The analytes may be in a whole blood sample, a blood serum sample, a blood plasma sample, other body fluids like ISF (interstitial fluid) and urine, and non-body fluids.

The test sensor 400 includes a fluid-receiving area (not shown) for receiving a fluid sample. A user may employ a lancet or a lancing device to pierce a finger or other area of the body to produce a fluid sample at the skin surface. The user may then collect this sample (e.g., blood sample) by placing the test sensor 400 into contact with the sample. The fluid-receiving area may contain a reagent that reacts with the sample to indicate the information related to an analyte in the sample, such as analyte concentration.

The test sensor 400 may be an electrochemical test sensor. An electrochemical test sensor typically includes a plurality of electrodes and a fluid-receiving area that contains an enzyme. The fluid-receiving area includes a reagent for converting an analyte of interest (e.g., glucose) in a fluid sample (e.g., blood) into a chemical species that is electrochemically measurable. The reagent typically contains an enzyme, such as glucose oxidase, which reacts with the analyte and with an electron acceptor such as a ferricyanide salt to produce an electrochemically measurable species that can be detected by the electrodes. Other enzymes may be used to react with glucose such as glucose dehydrogenase. In general, the enzyme is selected to react with the desired analyte or analytes to be tested so as to assist in determining an analyte concentration of a fluid sample. If the concentration of another analyte is to be determined, an appropriate enzyme is selected to react with the analyte.

Alternatively, the test sensor 400 may be an optical test sensor. Optical test sensor systems may use techniques such as transmission spectroscopy, absorption spectroscopy, diffuse reflectance, fluorescence spectroscopy, fluorescence resonance energy transfer, combinations thereof, and others for measuring the analyte concentration. An indicator reagent system and an analyte in a sample of body fluid react to alter light that is directed to the sensor 400. The degree of light alteration is indicative of the analyte concentration in the body fluid.

Some commercially available test sensors that may be used include those that are available commercially from Bayer HealthCare LLC (Tarrytown, N.Y.). These test sensors include, but are not limited to, those used in the Ascensia® CONTOUR® blood glucose monitoring system, the Ascensia® BREEZE® and BREEZE®2 blood glucose monitoring system, and the Ascensia® Elite® and Elite® XL blood glucose monitoring system. Other test sensors, in addition to the ones listed above, may be incorporated into the methods and systems of the present invention.

In FIG. 3, the meter 500 receives and engages the test sensor 400. The meter 500 measures the concentration of analyte for the sample collected by the test sensor 400. The meter 500 may include contacts for the electrodes to detect the electrochemical reaction of an electrochemical test sensor. Alternatively, the meter 500 may include an optical detector to detect the degree of light alteration for an optical test sensor. To calculate the actual concentration of analyte from the electrochemical or optical reaction measured by the meter 500 and to generally control the procedure for testing the sample, the meter 500 employs at least one processor 510, which may execute programmed instructions according to a measurement algorithm. Data processed by the processor 510 may be stored in memory 520. Furthermore, the meter may have a user interface 570 which includes a display (e.g., a liquid-crystal display or the like). Pushbuttons, a scroll wheel, touch screens, or a combination thereof, may also be provided as a part of the user interface 570 to allow a user to interact with the meter 500. The display typically shows information regarding the test results, the testing procedure and/or information in response to signals input by the user.

Although the meter 500 can store test results and provide a user interface 570 to display test results, the data-management software 210 on the portable device 200 provides more advanced functionality for managing, processing, and displaying test results and related information. Therefore, the test-related data collected by the meter 500 may be downloaded to the portable device 200 for use with the data-management software 210. In FIG. 3, the meter 500 includes an interface element 550 that enables the meter 500 to connect with the portable device 200 via the portable-device interface element 250.

The meter-interface element 550 and the portable-device interface element 250 may employ the interface technologies described previously. A USB interface may connect the portable device 200 with the meter 500. The transfer of data between the meter 500 and the portable device 200 may require a host function, such as the USB host function, to be employed on the portable device or meter 500, which includes a processor 510. As such, the download of data is managed by the portable device 200 or the meter 500 to execute appropriate software components stored on the meter 500 or the portable device 200. Data transferred, e.g., a series of blood-glucose readings, can be organized with timestamps or sequence numbers to ensure appropriate data storage and analysis by the portable device 200.

In addition to the interfaces described previously, other communication protocols for data transfer via interface elements 250 and 550 may be employed. For example, radio frequency identification (RFID) technology can provide an interface for data transfer to the portable device 200 from the meter 500. In particular, interface element 250 on the portable device 200 may include an RFID antenna and RFID circuitry. Meanwhile, the interface element 550 on the meter 500 may include the corresponding RFID circuitry, so that the meter 500 can be swiped past or scanned by the portable device 200 to transfer data, such as blood-glucose readings, to the portable device 200. Less power is required for the transmitter, e.g., the meter 500, and more power is required for the receiver, e.g., the portable device 200, to employ this RFID interface. In some embodiments, data in the range of about 56K to about 256K, which may correspond for example to about 100 blood-glucose readings, can be transferred at one time.

The RFID technique for transferring data may be employed between the portable device 200 and any other device, such as a processing device 100. As described previously, the processing device 100 may be a base-station processing device or a health care provider's processing device. Because these processing devices may already include the data-management software 210, the software 210 does not have to be launched from the portable device 200 and only stored data, such as data associated with blood-glucose readings, needs to be transferred to the processing device 100. In this embodiment, the interface element 150 on the processing device 100 includes the RFID antenna, as the processing device 100 acts as the receiver while the portable device 200 acts as the transmitter. Advantageously, less power is required for the portable device 200 in this embodiment.

The portable device 200 may have a power source such as a rechargeable battery 260, which may be recharged via the connection with the processing device 100 or another external device with a power supply. For example, power may be transferred via a USB connection between the processing device 100 and the portable device 200. When the portable device 200 and the meter 500 are connected, the battery 260 can be used to recharge the rechargeable battery 560 which powers the meter 500, or vice versa.

As described previously, the portable device 200 may connect to an intermediate device to receive field upgrades to the data and/or software stored on the portable device 200. The portable device 200 may also be used to update or add software to the meter 500. In an exemplary embodiment, a new or updated version of software for the meter 500 may be downloaded to the portable device 200. This may be accomplished after the portable device 200 connects to a remote download server through a networked PC or a mobile communications device. The new or updated version of software may then be downloaded to the meter 500 after the meter 500 is connected to the portable device 100. This download process may be managed by the portable device 200 or the meter 500.

Figure 4:
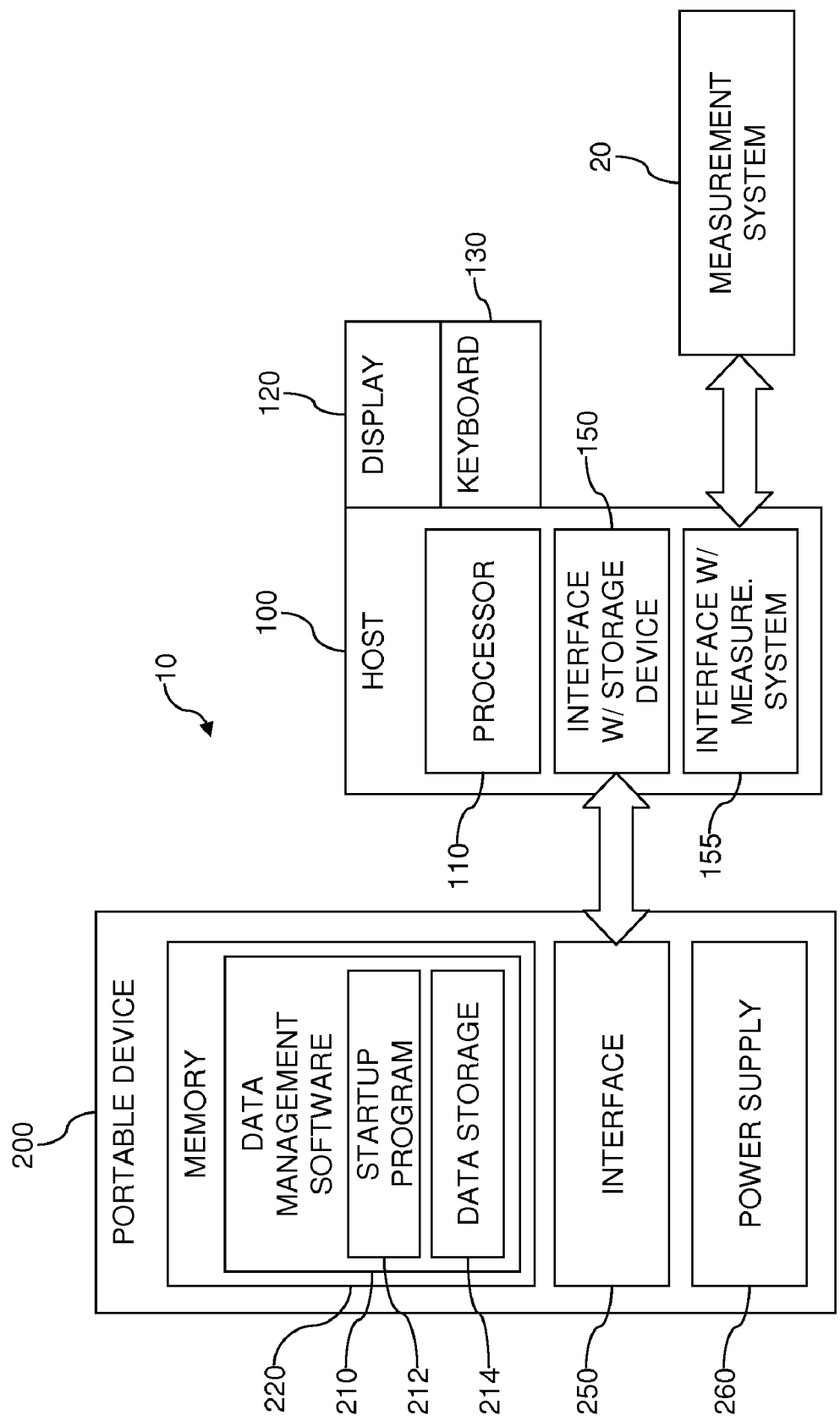
FIG. 4 illustrates a data-management system including a portable device and a measurement system both connected to the same processing device.

In FIG. 4, data collected by the measurement system 20 of FIG. 3 may be downloaded by connecting the measurement system 20 to the processing device 100 through processing-device interface element 155, while the portable device 200 is also connected to the processing device 100. The data can then be loaded onto the portable device 200 via the processing device 100. The connection between the measurement system 20 and the processing device 100 may employ the communication interface technologies described previously. For example, the measurement system 20 may be received into a second USB port on the processing device 100. In addition, the data-management software 210 running on the processing device 100 may be used to enable or facilitate the transfer of data from the measurement system 20.

Figure 5:
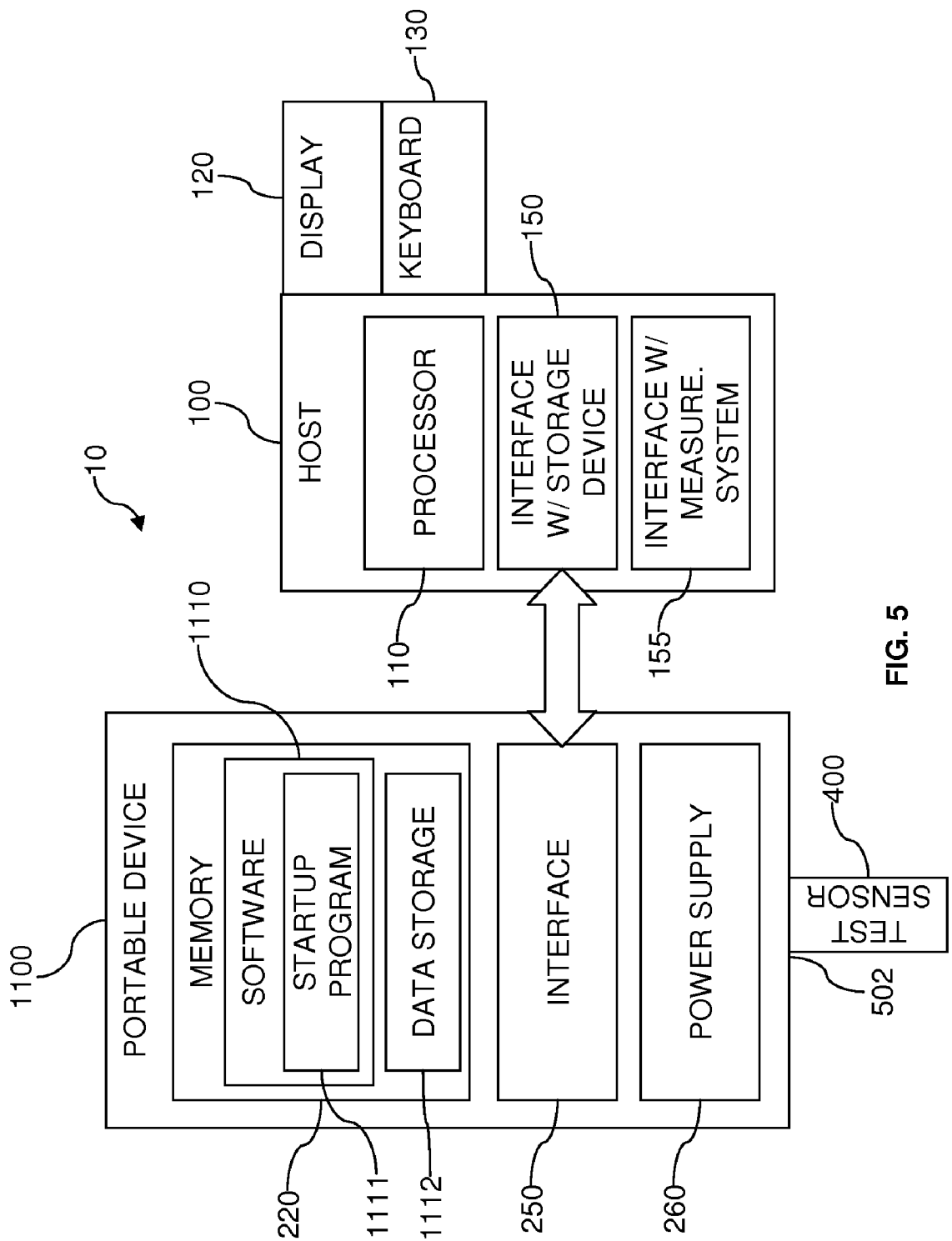
FIG. 5 illustrates a data-management system including a portable device that receives a test sensor and operates with a processor and a user interface of a processing device.

FIG. 5 illustrates another portable device 1100 that incorporates the components and functions of the portable device 200 with the components and functions of the meter 500. In particular, the portable device 1100 includes a memory 220 storing a software 1110 that may be launched on the processing device 100 without requiring the pre-installation of software components on the processing device 100. The software 1110 includes a startup program 1111 that launches the software 1110 on the processing device 100 in the manner described previously. In addition, the memory 220 may include data storage 1112, such as a database, that stores data collected or processed with the software 1110. The memory 220 may include a universal serial bus (USB) flash drive, a memory card, or the like. The portable device 1100 also has an interface element 250 that may connect to the interface element 150 of the processing device 100 via USB technology, RF technology, or the like.

In addition, the portable device 1100 may include a port 502 to receive an analyte-test sensor 400. A sample, such as a blood sample, may be collected by the test sensor 400 and may be analyzed as described previously to determine an analyte concentration, such as a blood glucose concentration. The software 1110 includes programmed instructions for analyzing the sample received with the analyte-test sensor 400. As such, when the software 1110 is launched on the processing device 100, the processor 110 on the processing device 100 executes the software 1110 to collect and analyze information from the detection of an electrochemical or optical reaction when the sample reacts with a reagent on the test sensor 400. Once the processor 110 determines test results from analyzing the sample on the test sensor 400, the processing device 100 may display the test results on the display 120 associated with the processing device 100. Accordingly, the portable device 1100 and the processing device 100 combine to provide a measurement system, such as a blood glucose meter, where the portable device 1100 provides the port 502 for detecting a reaction on the test sensor 400 and the processing device 100 analyzes the reaction with the software 1110 from the portable device 1100 and displays the test results. Additionally, the software 1110 may include features of the data-management software 210 described previously to provide enhanced data processing and display features on the processing device 100.

The memory 220 of portable device 1100 may include a Secure Digital (SD) card and the portable device 1100 may connect with a processing device 100, such as a PALM® handheld or Blackberry® device, via SDIO (Secure Digital Input Output) interface specifications. The portable device 1100 may therefore have the form of a SD card with the port 502 for receiving a test sensor 400, and the SD card can be plugged into a processing device 100 to provide a measurement system. Alternatively, the portable device 1100 may include other types of memory and may connect to the processing device via other technologies, such as Bluetooth® wireless technologies.

Additionally, the software 1110 may be Java based so that the portable device 1100 can use a web browser as commonly available on most operating systems to render, via HTML, a front-end user interface for the software 1110. Advantageously, the Java based software 1100 is generally not dependent on the operating system type, and many devices, such as a PALM® handheld or Blackberry® device, employ web browsers. Thus, the portable device 1100 provides a highly compatible and portable approach for converting many devices into a measurement system, such as a blood glucose meter. In general, the software launched by the portable devices described herein may also be Java based programs that are executable on web browsers and similar rendering applications.

Like the portable device 1100 of FIG. 5, an integrated device 600 in FIGS. 6A-6D incorporates the components and functions of the portable device 200 with the components and functions of the meter 500. Accordingly, the integrated device 600 may receive an analyte-test sensor 400 via the port 502. However, the integrated device 600 also includes a processor 610 that may calculate the concentration of analyte in the sample collected by the test sensor 400. Unlike the portable device 1100, the integrated device 600 does not require the calculation of analyte to be handled by a processor 110 of a separate processing device 100. Rather, the processor 610 in the integrated device 600 processes information from the detection of a reaction between the sample and a reagent on the test sensor 400. The test results are stored in the memory 220 of the integrated device 600. As such, the memory 220 may have a capacity in the range of about 500 MB to about 2 GB.

In addition, the integrated device 600 includes a user interface 670 that may be used to display the test results and to enter input for various display options. In particular, the user interface 670 may provide further convenience and portability for a data-management system 10 by integrating the functionality of the portable device 200 with advanced data processing and display features. In sum, the integrated device 600 integrates the portable device 200 with a user interface 670 as well as the components and functions of the meter 500.

Figure 6A:
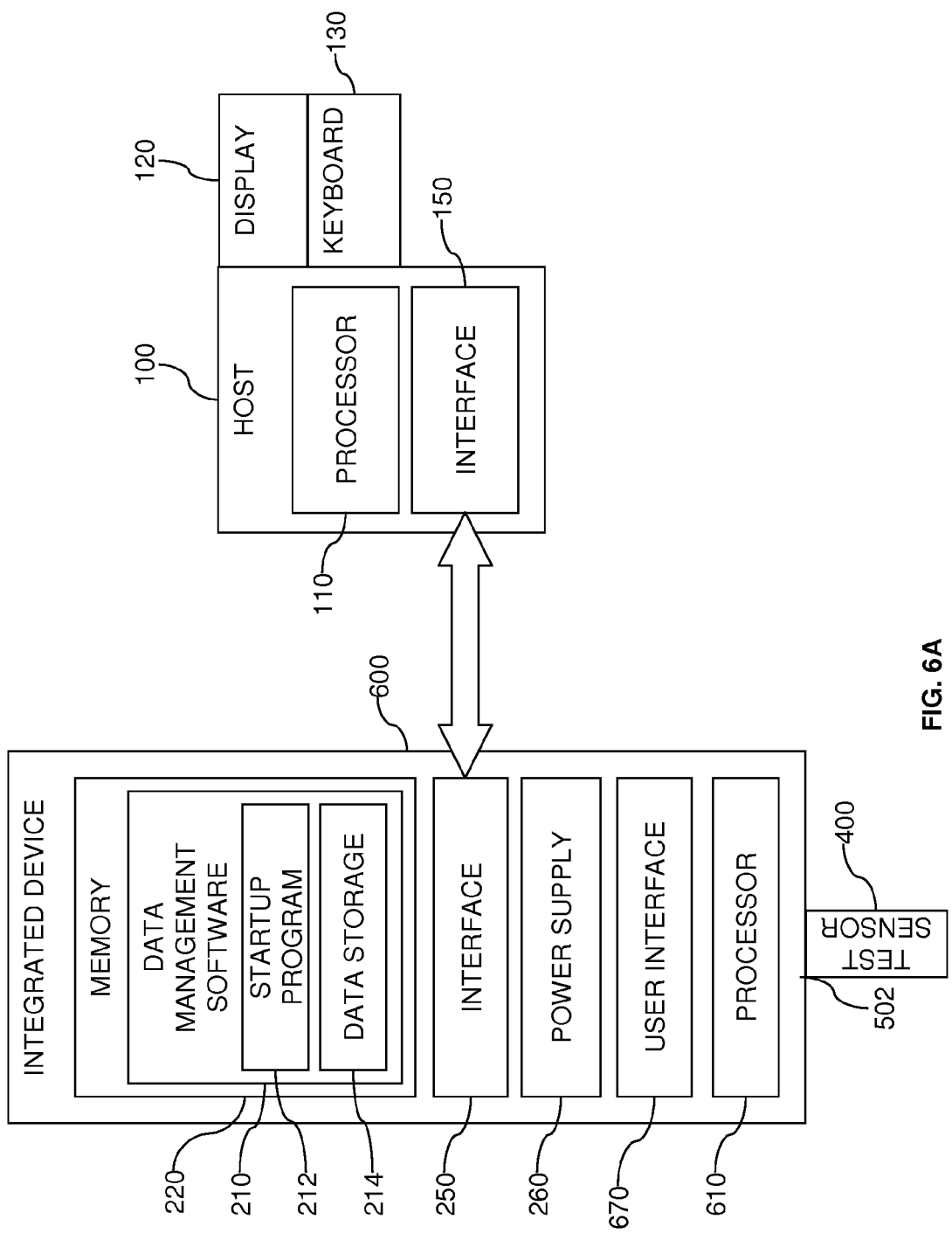
FIG. 6A illustrates a data-management system including an integrated device that provides a measurement system and a user interface.
Figure 6B:
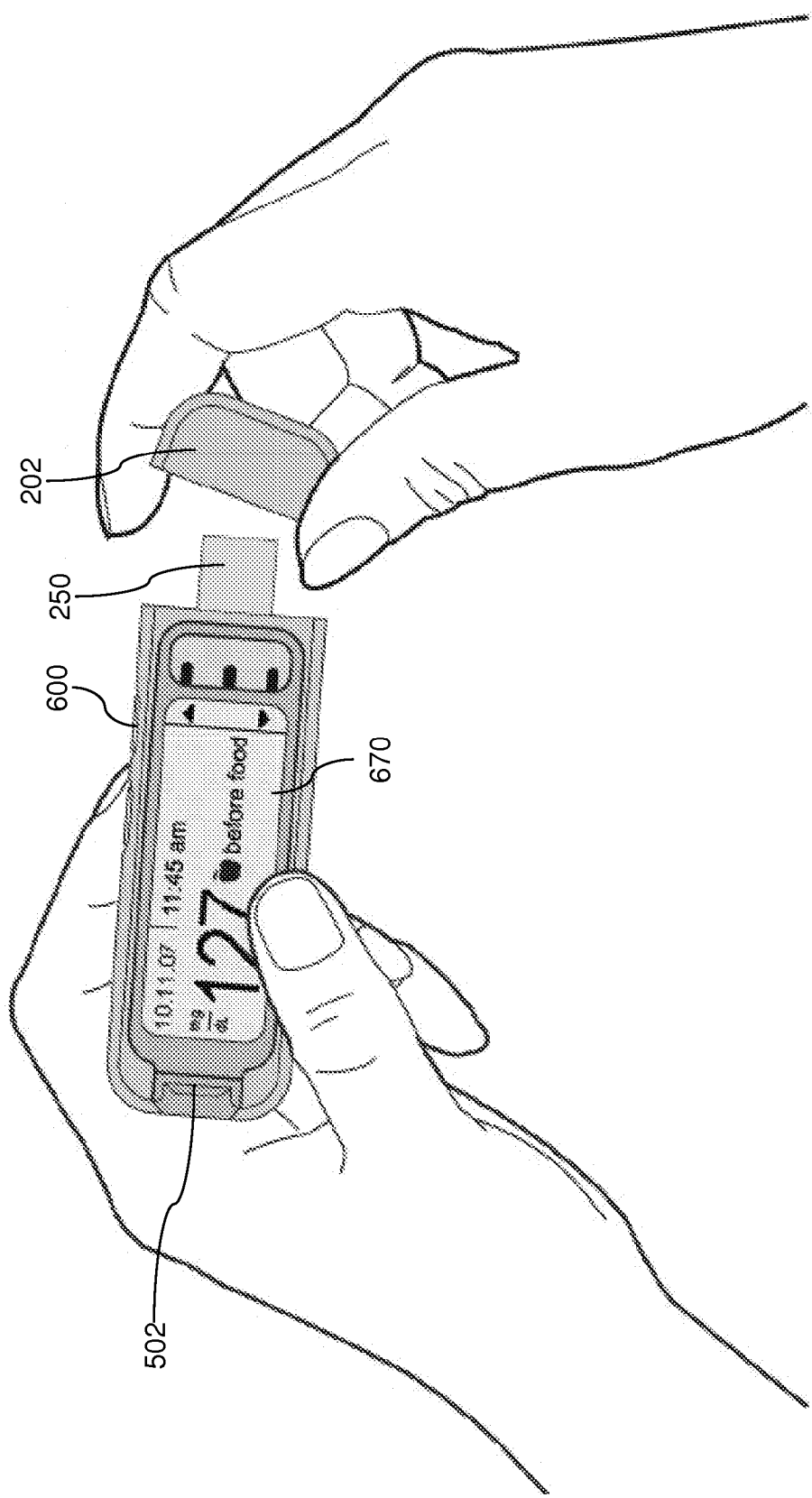
FIG. 6B illustrates the integrated device of FIG. 6A with a USB interface element.
Figure 6C:
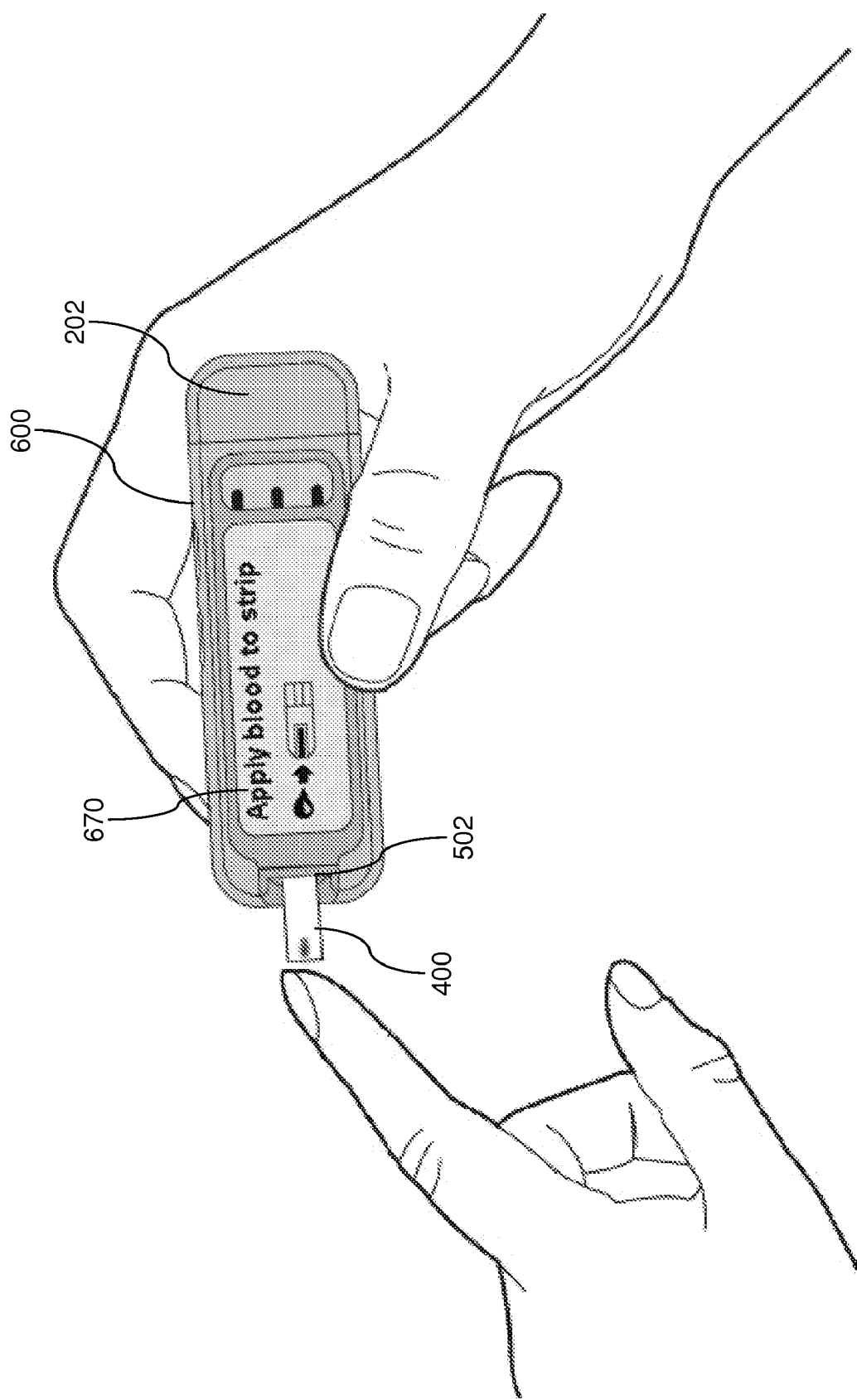
FIG. 6C illustrates the integrated device of FIG. 6A receiving a test sensor for receiving a sample.

Thus, as shown in FIGS. 6B and 6C, an integrated device 600 may be a portable blood glucose meter that provides data processing and display features. Users may employ the integrated device 600 to provide a blood sample via test sensor 400 and may access more sophisticated presentations of blood glucose test data from the integrated device 600 without launching the data-management application on a separate processing device 100.

Figure 6D:
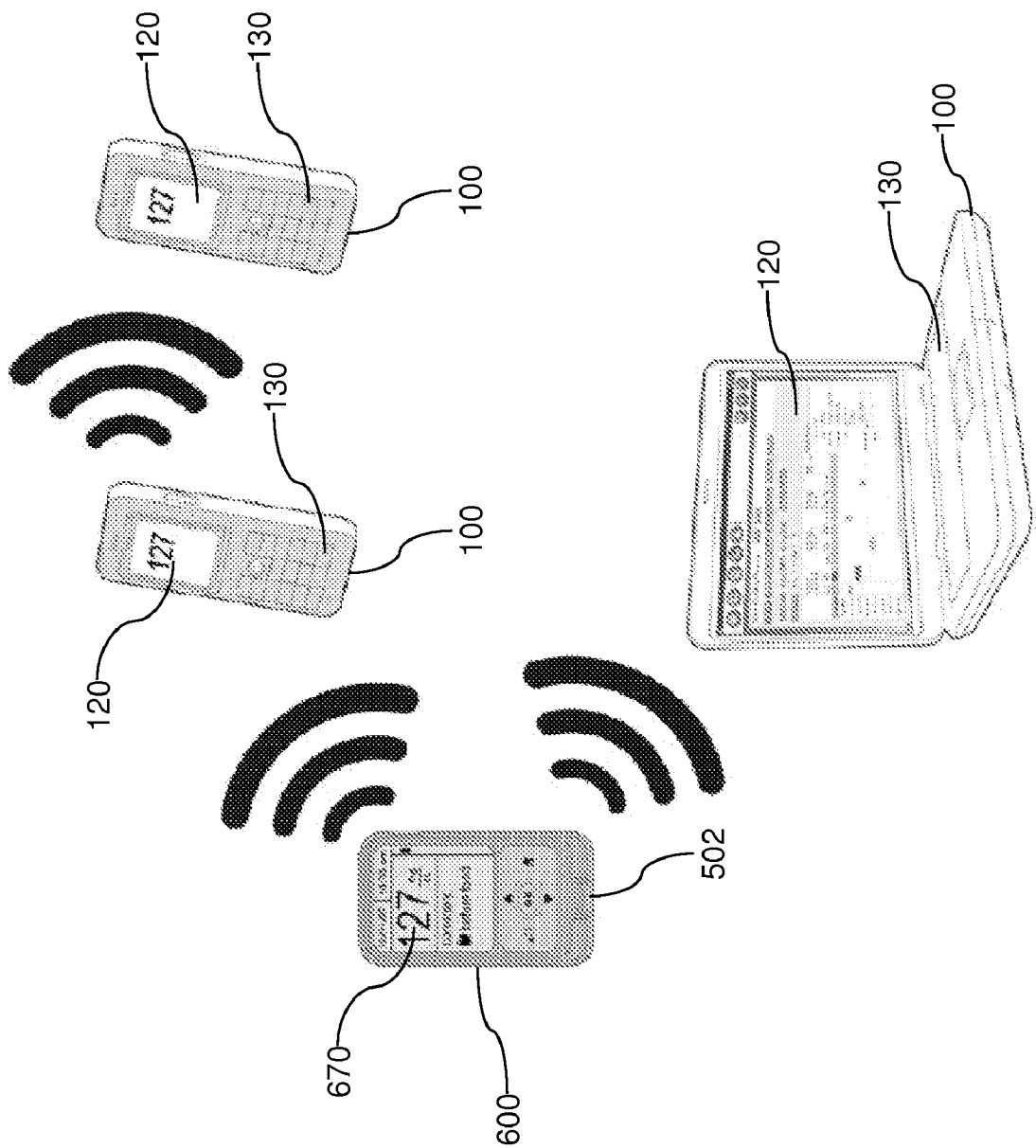
FIG. 6D illustrates the integrated device of FIG. 6A connected wirelessly to a plurality of processing devices.

However, as hardware limitations may still prevent all desired functionality to be incorporated into the integrated device 600, the integrated device 600 retains the ability to launch the data-management application on a larger processing device 100 and to provide the user with functionality not available on the integrated device. FIG. 6D illustrates the integrated device 600 connected wirelessly to more than one processing device 100, including a laptop PC and mobile communication devices.

As described above, the integrated device 600 may communicate with, and transfer data to, a processing device 100 without necessarily launching the software 210. Indeed, the processing device 100 may already include the data-management software 210. In particular, the RFID technique for transferring data can be employed between the integrated device 600 and the processing device 100. The interface element 150 of the processing device 100 includes the RFID antenna, as the processing device 100 acts as the receiver while the integrated device 600 acts as the transmitter. The integrated device 600 may be swiped past or scanned by the processing device 100 to transfer data, such as blood-glucose readings, to the processing device 100. Less power is required for the integrated device 600, and more power is required for the processing device 100. Data transferred, e.g., a series of blood-glucose readings, can be organized with timestamps or sequence numbers to ensure appropriate data storage and analysis by the processing device 100.

In further applications, the integrated device 600 may transmit data to a processing device 100 that resides remotely on a network. As described previously, various approaches can be implemented to provide networked communications. For example, the integrated device 600 may connect to an intermediate device, such as a PC with access to the Internet or a mobile communications device with access to a cellular network, to transmit data remotely to other systems or devices. In other embodiments, the integrated device 600 may communicate more directly with a remote system or device. For example, a remote processing device 100 may be a server in a centralized health care system that provides further processing or storage of data collected by the integrated device 600. The centralized health care system may provide a web-based or a client-server based front end to data-management software 210 running on the remote processing device 200. Additionally or alternatively, the data may be shared with health care professionals. Accordingly, to transfer data from the integrated device 600 to the remote processing device 100, the integrated device 600 may connect directly via the interface element 250, for example, to a wireless network or a Wi-Fi hotspot. Data encryption and authentication procedures may be employed to ensure data security. In one embodiment, the integrated device 600 detects the presence of a wireless network or a Wi-Fi hotspot and automatically transfers data to the remote processing device 100 through a background process. Alternatively, the integrated device 600 may alert the user via the user interface 670 that access to the remote processing device 100 is available, and the user can initiate data transfer if desired.

The integrated device 600 may store a display state for the user interface 670. For example, functionality may be available on the integrated device 600 to log testing information and a log book may be displayed on the display of user interface 670. The log book function may be accessed by selecting a shortcut icon on the screen or selecting the function through a menu. However, for convenience, when the user displays the logbook, the integrated device 600 tracks the state of the display, so that if the device 600 is powered off, enters a standby mode, or is otherwise deactivated during the logbook function, the logbook function and display can be started automatically when the device 600 is activated again. Of course, the display state may also be used for any other function that appears on the display.

Moreover, the display state stored by the integrated device 600 may be used with data-management software 210 that runs on the processing device 100. In particular, the user may display some information, such as a summary of test results, through the user interface 270 of the integrated device 600. If this particular display remains in the display state, the display state may be communicated to the data-management software 210 on the processing device 100 when it is connected to the integrated device 600, so that functionality in the data-management software 210 that corresponds to the display last shown on the device 600 may be automatically started. The data-management software 210 may automatically start a screen that provides detailed data regarding a summary of test results displayed on the integrated device 600.

In general, the portable device 200 may be integrated with varying levels of functionalities, such as user interface features and measurement system capabilities. However, any device employing components and functions of the portable device 200 may include a user interface, even if it does not incorporate components and functions of the meter 500.

FIGS. 7A-10B illustrate additional features that may be employed with the exemplary embodiments described previously. Although these features are described with respect to embodiments with a USB interface element 250, the features may be applied to embodiments employing other communication protocols for interface element 250, as discussed previously.

Figure 7A:
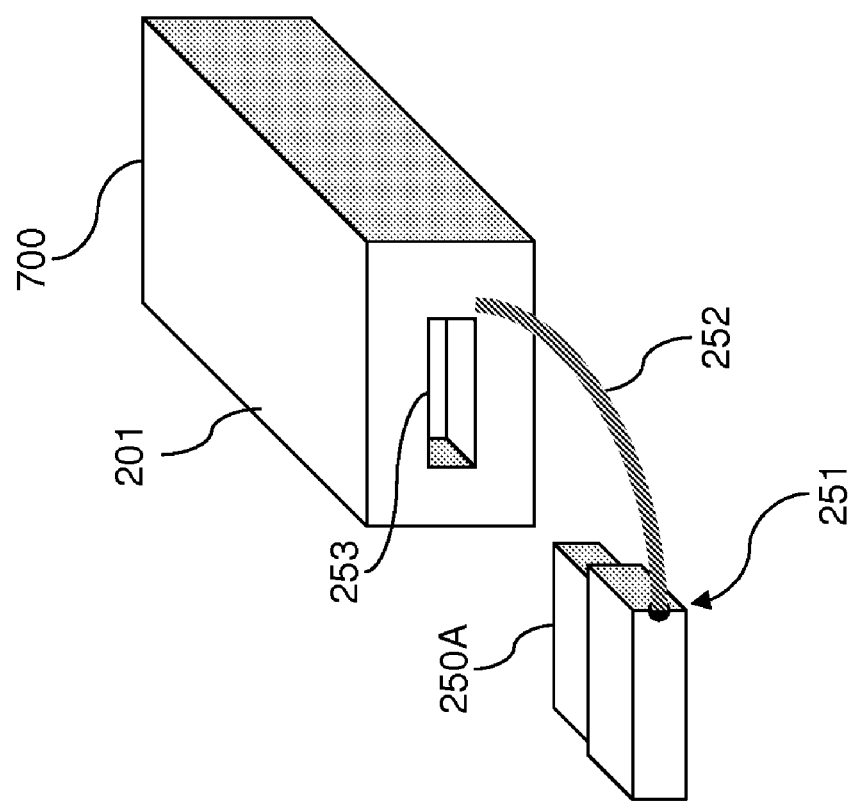
FIG. 7A illustrates a portable device with a USB interface element on an extendible cable.
Figure 7B:
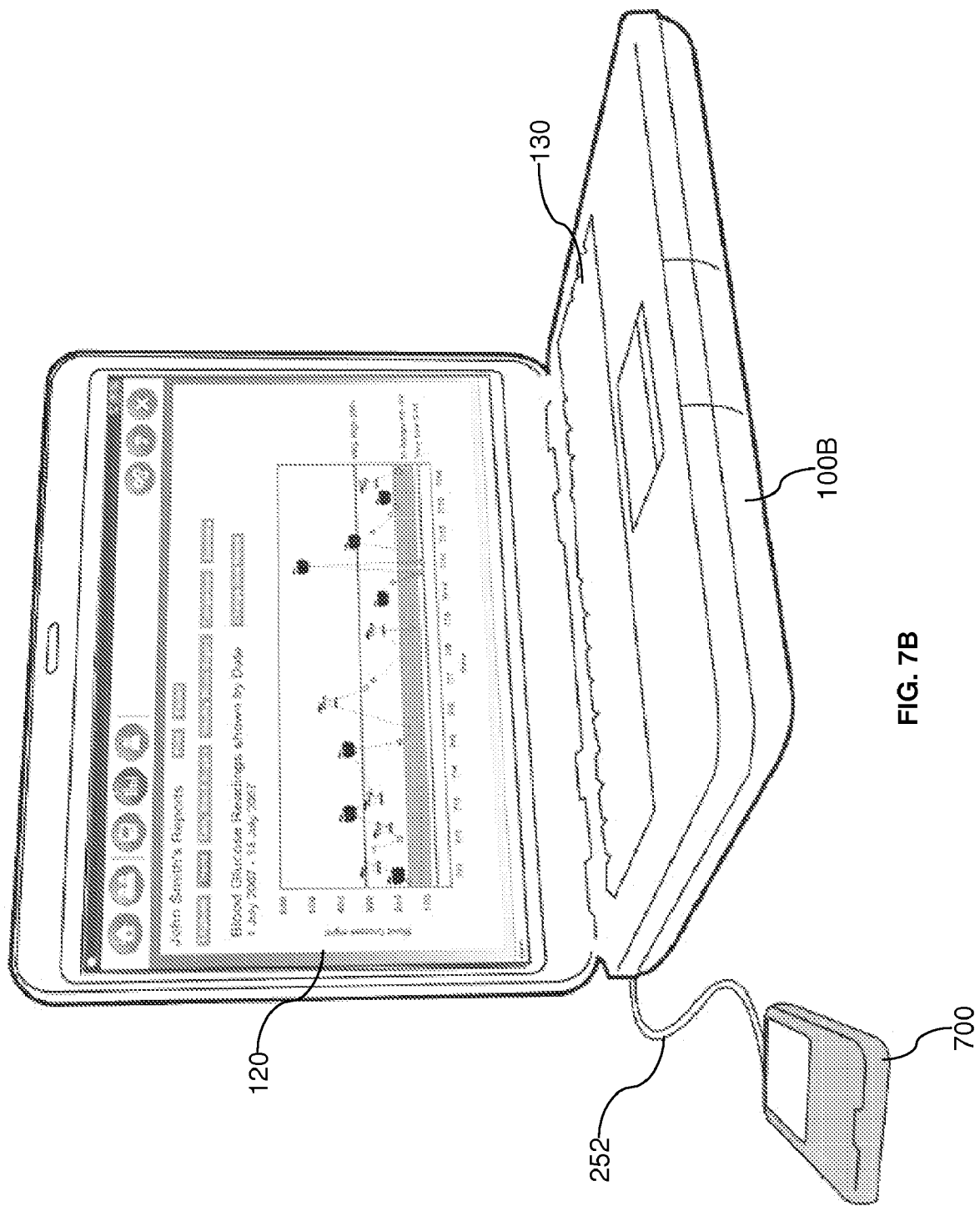
FIG. 7B illustrates a system with the portable device of FIG. 7A connected to a processing device.

FIGS. 7A and 7B illustrate a portable device 700 which may be similar in many respects to the portable device 200 described previously. The portable device 700 includes a USB interface element 250A that may extend from the body, or a housing portion, of the portable device 700 to keep the body from physically interfering with the insertion of the interface element 250A into a USB port of a processing device 100. In particular, a conducting cable 252 of convenient length extends between the interface element 250A and the body 201 of the portable device 700. The conducting cable 252 enables the interface element 250A to communicate electrical signals to other components of the portable device 700, while the interface element 250A is spaced away from the body 201 of the portable device 700. To provide convenient storage of an unnecessary length of the conducting cable 252, a portion of the interface element 250A includes a storage chamber 251. The storage chamber 251 of FIG. 7A includes a spring-loaded cable recoil with a clutch, which draws any slack in the conducting cable 252 into the storage chamber 251. The conducting cable 252 maintains an appropriate amount of tension, and an additional length of the conducting cable 252 can be easily drawn from the storage chamber 251 when extra length is required. When the interface element 250A is not in use, it can be conveniently stored in the storage cavity 253 in the body 201 of the portable device 700. FIG. 7B illustrates the portable device 700 connected via conducting cable 252 to a processing device 100B, which is a laptop PC.

Figure 8A:
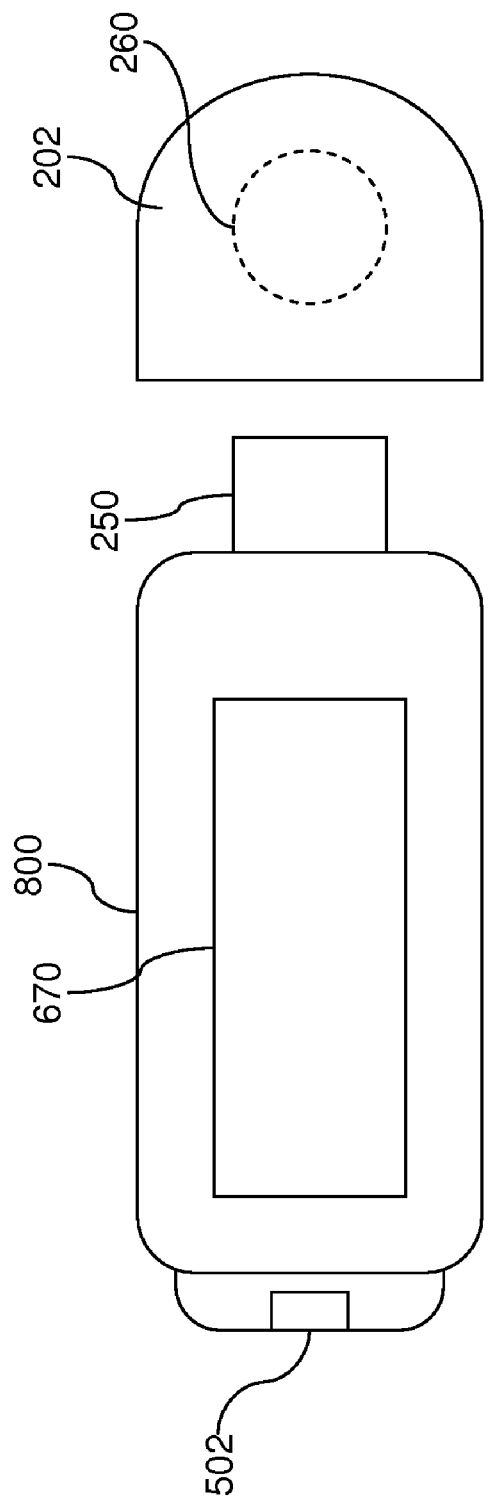
FIG. 8A illustrates a view of a portable device with a battery pack stored in an end cap.
Figure 8B:
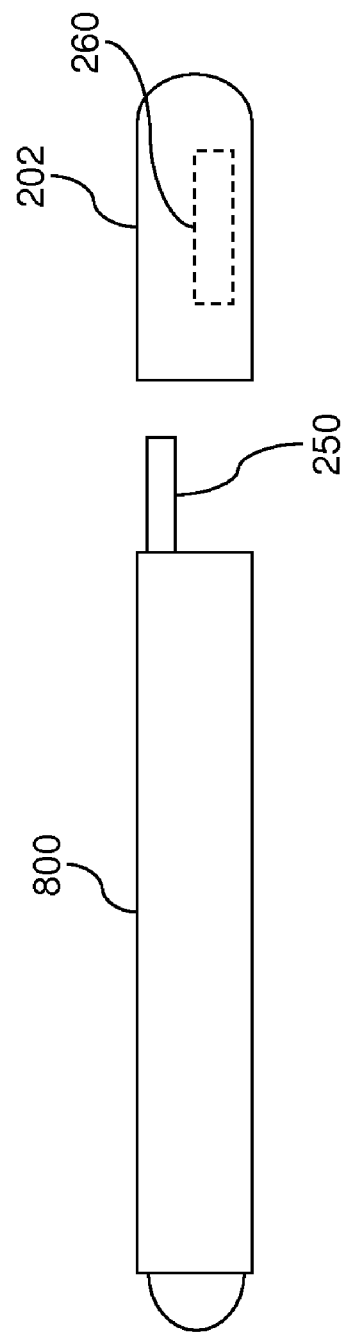
FIG. 8B illustrates another view of the portable device of FIG. 8A.

FIGS. 8A and 8B illustrate an integrated device 800, which may be similar in many respects to the integrated device 600. The integrated device 800 has a USB interface element 250. The integrated device 800 may be powered by a connection via the USB interface element 250 to either a processing device 100, such as a PC, or to a battery pack 260. In FIGS. 8A and 8B, the battery pack 260 is disposed in a cap 202 which fits over the USB interface element 250. Thus, aesthetically, the battery pack 260 looks like a cap for the USB interface element 250. The battery pack 260 may be positioned within the cap 202 according to a first orientation, so that when the cap 202 is placed over the USB interface element 250, the battery pack 260 connects with the USB interface element 250 and provides power to the integrated device 800. FIG. 8B illustrates the cap 202 in a second orientation where the battery pack 260 is disposed in an offset position so that the battery pack 260 and the USB interface element 250 are not aligned. Thus, when in the second orientation, the battery pack 260 does not connect to the USB interface element 250, enabling the battery power to be saved and the battery life to be extended. The cap 202 may be transitioned between the first orientation and the second orientation by removing the cap 202, turning the cap 202 180-degrees, and placing the cap 202 back over the interface element 250. The battery pack 260 may include one or more replaceable batteries. Alternatively, the batteries are not replaceable and are fixed to the cap 202, and thus, the entire cap 202 must be replaced to employ new batteries.

Figure 9A:
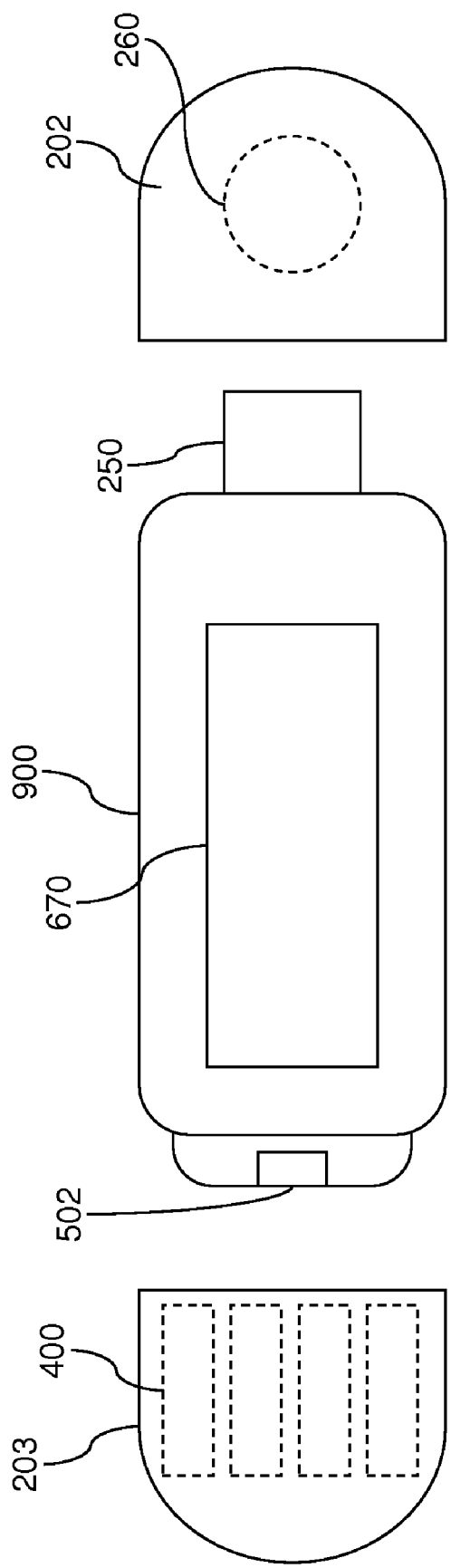
FIG. 9A illustrates a view of a portable device with a battery stored in a first end cap and sensor strips stored in a second end cap.
Figure 9B:
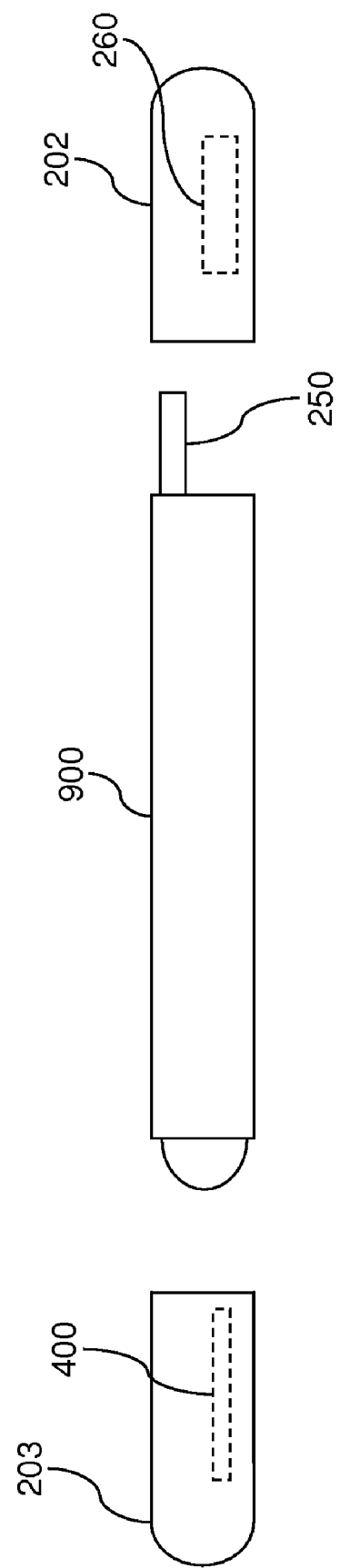
FIG. 9B illustrates another view of the portable device of FIG. 9A.

FIGS. 9A and 9B illustrate another integrated device 900, which may be similar in many respects to the integrated device 800 described previously. One end of the integrated device 900 includes an USB interface element 250 with a cap 202. Meanwhile, the other end of the integrated device 900 includes another cap 203 that stores test sensors 400. The caps 202 and 203 are interchangeable. Thus, during operation, the cap 202 is placed over the USB interface element 250 to connect the battery pack 260 to deliver power, and the cap 203 is removed to provide access to the sensor strips 400 for collecting samples. For example, the cap 203 may hold multiple test sensors 400 that may be used to collect samples, and the test sensors 400 may then interface with the integrated device 800 to capture the sample data. However, when the integrated device 800 is not in use, the cap 203 may be placed over the USB interface element 250, and the cap 202 may be placed over the other end of the integrated device 800. The cap 203 may provide a sealing fit over the ends of the integrated device 800 to promote proper storage of the test sensors 400.

FIG. 10A illustrates yet another integrated device 1000, which may be similar in many respects to the integrated device 600. The integrated device 1000 includes a USB interface element 250 in a main body 201. A cap 209 may be removably coupled to the main body 201 and placed over the USB interface element 250. The cap 209 includes a temperature sensor 280 and corresponding circuitry 281. The temperature sensor 280 may include a thermocouple, thermistor, thermochromatic sensor, or the like. The temperature sensor 280 measures the temperature at, or near, an outer surface 204 of the cap 209. When the cap 209 is placed over the USB interface element 250, the temperature sensor 280 is connected to the interface element 250 and corresponding temperature data is transferred to the processor of the integrated device 1000. In general, the temperature of the main body 201 may not reflect the ambient temperature, because the main body 201 may retain heat generated by the operation of the integrated device 1000. The temperature of the main body 201 may also be affected by its proximity to other warm or cold bodies. For example, body heat may be transferred to the main body 201 when the integrated device 1000 is held in a user's hands or is otherwise carried in proximity to the user's body. Due to the thermal mass of the main body 201, the main body 201 may reach equilibrium with the ambient very slowly. Because the outer surface 204 of the cap 209 has a weak thermal coupling with the main body 201, however, the temperature measured at, or near, the outer surface 204 is not substantially affected by the main body 201. Moreover, the temperature of the temperature sensor 280 reaches equilibrium with the ambient more quickly than the main body 201. A heat sink may be employed to speed up the transition to ambient temperature for the outer surface 204. As a result, the temperature sensor 280 reflects the ambient temperature more accurately. The temperature data from the temperature sensor may be employed to determine the concentration of an analyte in a fluid sample (e.g., blood glucose concentration) according to a reaction with the reagent on the test sensor 400. Because the level of reaction may be affected by changes in temperature of the reagent, the ambient temperature can be measured to estimate the temperature of the reagent. As such, the integrated device 1000 may account for the reagent's sensitivity to temperature and, thus, obtain a more accurate calculation of the concentration of analyte in the sample.

FIG. 10B illustrates a cross-section of a cap 209 with a temperature sensor 280 that may be employed with the integrated device 1000 of FIG. 10A. In particular, the temperature sensor 280 includes a thin membrane 205 in a part of an outer wall portion 206 of the cap 209. The thin membrane 205 has a low thermal mass and a large area-to-thickness ratio that helps the thin membrane to reach equilibrium with the ambient more quickly. As such, the temperature sensor 280 measures the temperature of the thin membrane 205 to achieve a more accurate determination of the ambient temperature. To minimize heat conduction to the thin membrane 205, the thin membrane 205 may be formed of plastic or the like, and the outer wall portion 206 may be coupled to the rest of the cap 209, so that there is at least one gap 207 between the outer wall portion 206 and the rest of the cap 209. The gap 207 allows ambient air flow around the thin membrane 205 to promote transition by the thin membrane to the ambient temperature. Alternatively, the outer wall portion 206 may provide a very loose interlocking connection that includes gaps 207 and allows ambient airflow around the thin membrane 205. The thin membrane 205 or the outer wall portion 206 may be replaced if either experiences any damage. The temperature sensor circuitry 281 may include an infrared (IR) sensor to measure the temperature of the thin membrane 205. Alternatively, the thin membrane 205 may include a thermochromic material, which changes color with temperature. The temperature sensor 280 in this case may include a light source, such as one or more laser LED's, and a detector, such as one or more photodiodes. The light source transmits photons to the thermochromic material, and the detector receives the photons that are reflected from the thermochromic material and that indicate the color of the thermochromic material. In some embodiments, the circuitry 281 may be housed in the main body 281 rather than the cap 209, while the thin membrane 205 or other temperature sensor structure remains in the cap 209.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention.

What we claim is:

1. A device for managing health data, comprising:
   a housing portion including a health data management system and a data communications element that provides data communications between the health data management system and an external processing device, the health data management system including a meter for measuring a reaction between a reagent and an analyte in a user sample to determine an analyte concentration in the user sample; and a cap that is removably coupled to the housing portion, the cap including a temperature sensor that provides a measurement of ambient temperature to the health data measurement system, and wherein a level of the reaction between the reagent and the analyte is affected by a temperature of the reagent, the health data management system estimates the temperature of the reagent from the measurement of ambient temperature provided by the temperature sensor, and the health management system determines the analyte concentration of the user, and wherein a weak thermal coupling between the housing portion and the cap minimizes heat transfer therebetween so that the cap maintains a cap temperature that is closer to the ambient temperature than the housing portion.

2. The device of claim 1, wherein the cap is placed over the data communications element of the housing portion, and the temperature sensor measures the ambient temperature at or near a surface of the cap.

3. The device of claim 2, wherein the data communications element is a USB interface element, and the cap is removably placed over the USB interface element.

4. The device of claim 2, wherein, when the cap is placed over the data communications element of the housing portion, the temperature sensor of cap is connected to the data communications element and transfers temperature data to the health data management system via the data communications element.

5. The device of claim 1, wherein the temperature sensor measures the ambient temperature of a thin membrane in an outer wall portion of the cap.

6. The device of claim 5, wherein the thin membrane is formed of plastic.

7. The device of claim 5, wherein the outer wall portion is coupled to the rest of the cap to define a gap between the outer wall portion and the rest of the cap, the gap allowing ambient air to flow around the thin membrane to allow the thin membrane to achieve equilibrium with the ambient temperature.

8. The device of claim 5, further comprising temperature circuitry that determines the measurement of ambient temperature with the temperature sensor, and the temperature circuitry includes an infrared sensor that measures the temperature of the thin membrane.

9. The device of claim 1, wherein the temperature sensor includes a thermocouple, thermistor, or a thermochromatic sensor.

10. The device of claim 1, wherein the thin membrane includes a thermochromic material and the temperature sensor includes a light source and a detector to determine the temperature of the thermochromic material.

11. The device of claim 1, wherein cap has a thermal mass that is less than the first housing portion.

12. The device of claim 1, wherein the cap reaches equilibrium with the ambient temperature more quickly than the first housing portion.

13. The device of claim 1, further comprising a heat sink to which the cap transfers heat to achieve equilibrium with the ambient temperature.

14. The device of claim 1, further comprising temperature circuitry that determines, with the temperature sensor, the measurement of ambient temperature, and the temperature circuitry is disposed in the housing portion.

* * * * *

UNITED STATES PATENT AND TRADEMARK OFFICE
CERTIFICATE OF CORRECTION

| | | |
|---|---|---|
| PATENT NO. | : 8,401,873 B2 | Page 1 of 1 |
| APPLICATION NO. | : 12/129562 | |
| DATED | : March 19, 2013 | |
| INVENTOR(S) | : Brown et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 919 days.

Signed and Sealed this
Second Day of December, 2014

Michelle K. Lee
*Deputy Director of the United States Patent and Trademark Office*